United States Patent
Baba et al.

(10) Patent No.: US 8,597,191 B2
(45) Date of Patent: Dec. 3, 2013

(54) ULTRASONIC IMAGING APPARATUS AND A METHOD OF GENERATING ULTRASONIC IMAGES

(75) Inventors: Tatsuro Baba, Otawara (JP); Naohisa Kamiyama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1309 days.

(21) Appl. No.: 12/327,190

(22) Filed: Dec. 3, 2008

(65) Prior Publication Data

US 2009/0149759 A1    Jun. 11, 2009

(30) Foreign Application Priority Data

Dec. 5, 2007    (JP) .................................. 2007-314991

(51) Int. Cl.
*A61B 8/00*    (2006.01)
(52) U.S. Cl.
USPC ........................................................ 600/453
(58) Field of Classification Search
USPC ................ 600/453, 437, 441, 443, 448, 456;
382/128, 262, 270, 272
See application file for complete search history.

(56) References Cited

U.S. PATENT DOCUMENTS

| 4,559,952 A | 12/1985 | Angelsen et al. |
| 5,433,206 A | 7/1995 | Sabbah et al. |
| 5,642,732 A * | 7/1997 | Wang ............................. 600/453 |
| 2006/0052704 A1 | 3/2006 | Baba et al. |
| 2007/0167790 A1 * | 7/2007 | Kim et al. ..................... 600/454 |

FOREIGN PATENT DOCUMENTS

| JP | 6-181927 A | 7/1994 |
| JP | 2004-242986 A | 9/2004 |

OTHER PUBLICATIONS

Japanese Office Action issued Jun. 26, 2012 in patent application No. 2007-314991.
U.S. Appl. No. 12/176,461, filed Jul. 21, 2008, Tatsuro Baba, et al.

* cited by examiner

*Primary Examiner* — Elmer Chao
(74) *Attorney, Agent, or Firm* — Oblon, Spivak, McClelland, Maier & Neustadt, L.L.P.

(57) ABSTRACT

A processor generates a first Doppler spectrum image representing the velocity of a moving body at each observation point by analyzing the frequency of signals received at the plurality of observation points acquired via Doppler scanning. An interpolator acquires a second Doppler spectrum image consecutively at each observation point time when the ultrasound has not been transmitted to and received from each observation point by the Doppler scanner transmitting and receiving the ultrasound toward and from the plurality of observation points at a plurality of respective times, based on interpolation of the first Doppler spectrum image at each observation point. The interpolator generates a third Doppler spectrum at each observation point by combining the first Doppler spectrum at each observation point and the second Doppler spectrum image at each observation point per observation point.

9 Claims, 15 Drawing Sheets

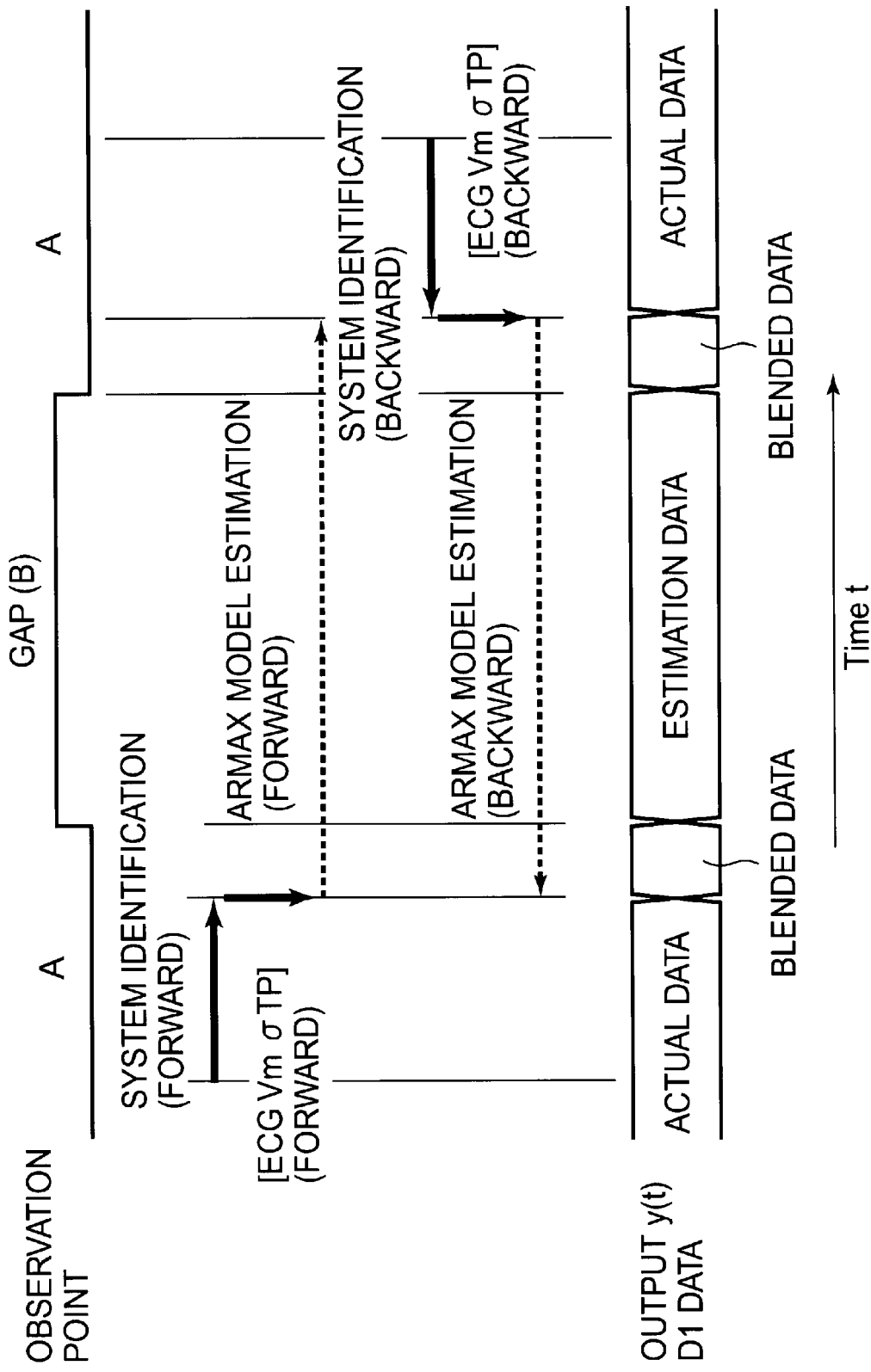

FIG. 14
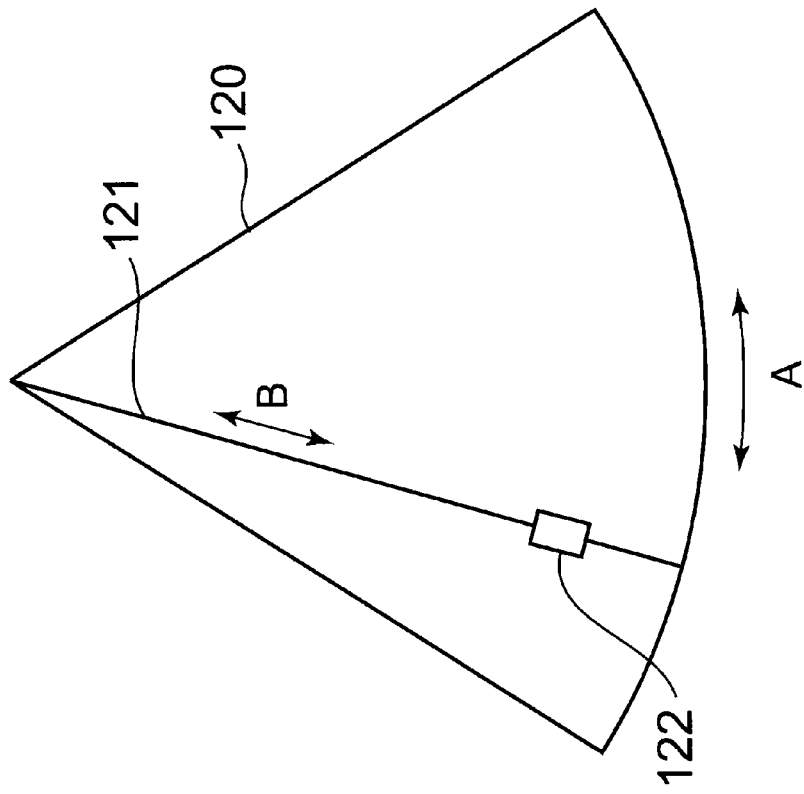
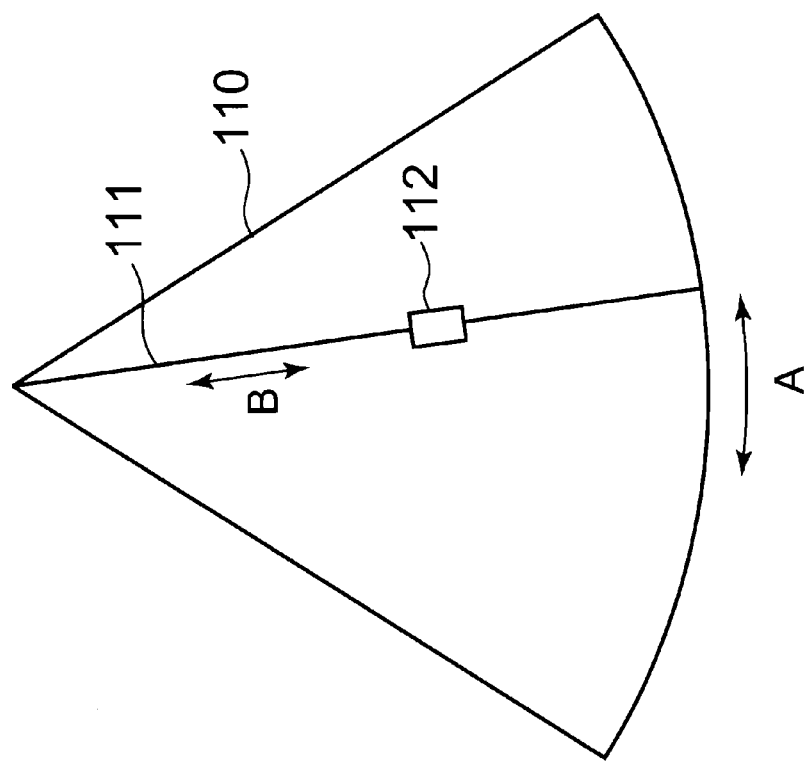

_US 8,597,191 B2_

ULTRASONIC IMAGING APPARATUS AND A METHOD OF GENERATING ULTRASONIC IMAGES

BACKGROUND OF THE INVENTION

1. Field of the Invention

The present invention relates to an ultrasonic imaging apparatus that captures Doppler spectrum images of a plurality of sites and a method of generating ultrasonic images thereby.

2. Description of the Related Art

Ultrasonic imaging apparatuses that obtain blood flow information from a diagnostic site by means of an ultrasonic Doppler method are known. When ultrasound is directed toward a certain diagnostic site with a flow such as blood flow in a subject, the received frequency shifts slightly, relative to the transmission frequency due to the Doppler effect. This Doppler shift frequency is proportional to the blood flow velocity. Blood flow information is obtained by analyzing the Doppler shift frequency. For example, a technique has been adopted for observing time changes in the blood flow information by implementing the pulsed wave Doppler method (PWD) or continuous wave Doppler method (CWD).

The ultrasonic imaging apparatus performs fast Fourier Transform (FFT) for obtained Doppler signals. Then, the ultrasonic imaging apparatus displays a spectrum of the results of that frequency analysis with the frequency f (velocity v) on the vertical axis and time t on the horizontal axis. Directed toward that Doppler spectrum image, various items used in diagnosis are measured.

The function of the heart (cardiac function) has been evaluated by utilizing the ultrasonic Doppler method. For example, by measuring the velocity of left ventricular inflow and the velocity of left ventricular outflow, indices such as left ventricular ejection fraction (E/F) and Tei-Index (Total Ejection Isovolume Index) are obtained in order to evaluate the cardiac function.

Conventionally, the electrocardiographic waveform of a subject is acquired in order to identify the time phase when the left ventricular inflow occurs and the time phase when the left ventricular outflow occurs. Then, indices such as the left ventricular ejection fraction (E/F) are derived by separately measuring the velocity of the left ventricular inflow and the velocity of the left ventricular outflow. In other words, the velocity of the left ventricular inflow and the velocity of the left ventricular outflow are obtained from separate heartbeats in order to obtain the indices described above.

When the left ventricular inflow and left ventricular outflow are obtained from separate heartbeats, it is necessary to recalculate indices such as the abovementioned left ventricular ejection fraction (E/F) by combining the index obtained from measuring the left ventricular inflow and that obtained from measuring the left ventricular outflow.

Therefore, the operation is very complicated. In addition, the left ventricular inflow and left ventricular outflow are measured via different heartbeats, so there is a problem in which indices such as the left ventricular ejection fraction (E/F) become instable or the reproducibility of the indices becomes poor when the heart rate varies.

Moreover, even when the average value of the indices acquired from a plurality of heartbeats is obtained, the accuracy thereof may be insufficient.

In addition, there is an alternative method to set range gates (observation points) at a plurality of sites to acquire the blood flow information at a plurality of sites (e.g., Japanese published examined application H3-203706 and U.S. Pat. No. 3,180,958). For example, blood flow information at two sites is acquired by setting the range gates at the two sites and alternately transmitting and receiving ultrasound toward and from respective sites once each. For example, blood flow information at observation point A is acquired by transmitting and receiving the ultrasound toward and from observation point A once, and subsequently, blood flow information at observation point B is acquired by transmitting and receiving ultrasound toward and from observation point B. Later, by alternately transmitting and receiving ultrasound toward and from observation point A and observation point B once each, blood flow information at each observation point is alternately acquired.

However, as in the method according to the prior art, when ultrasound is alternately transmitted toward and received from a plurality of sites once each, the pulse repetition frequency (PRF) corresponding to the sampling frequency becomes smaller, depending on the number of range gates (observation points). Therefore, there is a problem in which the Doppler velocity range of a Doppler spectrum image becomes small, resulting in an aliasing phenomenon (folding phenomenon). Thus, the method according to the prior art is not suitable for measuring the circulatory system.

For example, when ultrasound is alternately transmitted toward and received from two sites once each, the pulse repetition frequency PRF becomes half. Therefore, the Doppler velocity range becomes half, and a folding phenomenon occurs. Specifically, if the blood flow velocity is 60 cm/s when the pulse repetition frequency PRF is 4 kHz and the sight depth is 15 cm, the Doppler spectrum image becomes subject to a folding phenomenon.

In addition, conventionally, the blood flow information at each observation point is acquired by setting a plurality of range gates (observation point) on the same scanning line. In this case, because observation points can only be set on the same scanning line, it is difficult to obtain the blood flow information at a plurality of observation points in the cardiac chambers. Therefore, this method is also unsuitable for measuring the circulatory system.

SUMMARY OF THE INVENTION

The present invention is intended to provide an ultrasonic imaging apparatus that can measure the flow rate of a moving body at each observation point without reducing the velocity range of the moving body at a plurality of observation points and a method of generating ultrasonic images thereby.

The first aspect of the present invention is a ultrasonic imaging apparatus comprising: a Doppler scanner configured to perform Doppler scanning by serially transmitting and receiving ultrasound toward and from each of a plurality of observation points in a subject at a plurality of respective times; a processor configured to generate a first Doppler spectrum image representing the velocity of a moving body at each observation point by analyzing the frequency of signals received at the plurality of observation points acquired via Doppler scanning; an interpolator configured to acquire a second Doppler spectrum image at each observation point when the ultrasound has not been transmitted to and received from each observation point by the Doppler scanner transmitting and receiving ultrasound toward and from the plurality of observation points at a plurality of respective times, based on interpolation of the first Doppler spectrum image at each observation point generated by the processor, and to generate a third Doppler spectrum at each observation point by combining the first Doppler spectrum at each observation point generated by the processor and the second Doppler spectrum image at each observation point via interpolation for each observation point; and a display controller configured to cause the third Doppler spectrum image at each observation point combined by the interpolator to be displayed on a display.

According to the first aspect of the present invention, by serially transmitting and receiving ultrasound toward and from each of a plurality of observation points at a plurality of respective times, the flow rate of a moving body at each observation point can be measured without reducing the velocity range of the flow rate of the moving body at the plurality of observation points. In addition, for the time zone when the ultrasound has not been transmitted to and received from each observation point, consecutive Doppler spectrum images can be generated by interpolating the Doppler spectrum image at each observation point.

In addition, the second aspect of the present invention is a method of generating ultrasonic images, characterized by: performing Doppler scanning by serially transmitting and receiving ultrasound toward and from each of a plurality of observation points in a subject at a plurality of respective times; generating a first Doppler spectrum image representing the velocity of a moving body at each observation point by analyzing the frequency analysis of the signals received at the plurality of observation points acquired by the Doppler scan; acquiring a second Doppler spectrum image at each consecutive observation point when the ultrasound has not been transmitted to and received from each observation point by the Doppler scanner transmitting and receiving the ultrasound toward and from the plurality of observation points at a plurality of respective times, based on interpolation of the first Doppler spectrum image at each observation point generated by the frequency analysis, and generating a third Doppler spectrum at each observation point by combining the first Doppler spectrum at each observation point generated by the frequency analysis and interpolation of the second Doppler spectrum image at each observation point per observation point; and displaying the third Doppler spectrum image at each observation point that has been combined.

BRIEF DESCRIPTION OF THE DRAWINGS

FIG. 7 is a diagram for describing a process for interpolating a part with data missing in the Doppler spectrum.

FIG. 14 is a diagram for describing the second example of setting an observation point, the diagram illustratively showing a cross-sectional image.

DETAILED DESCRIPTION OF THE EMBODIMENTS

An ultrasonic imaging apparatus according to an embodiment of the present invention is described with reference to FIG. 1 and FIG. 2.

Figure 1:
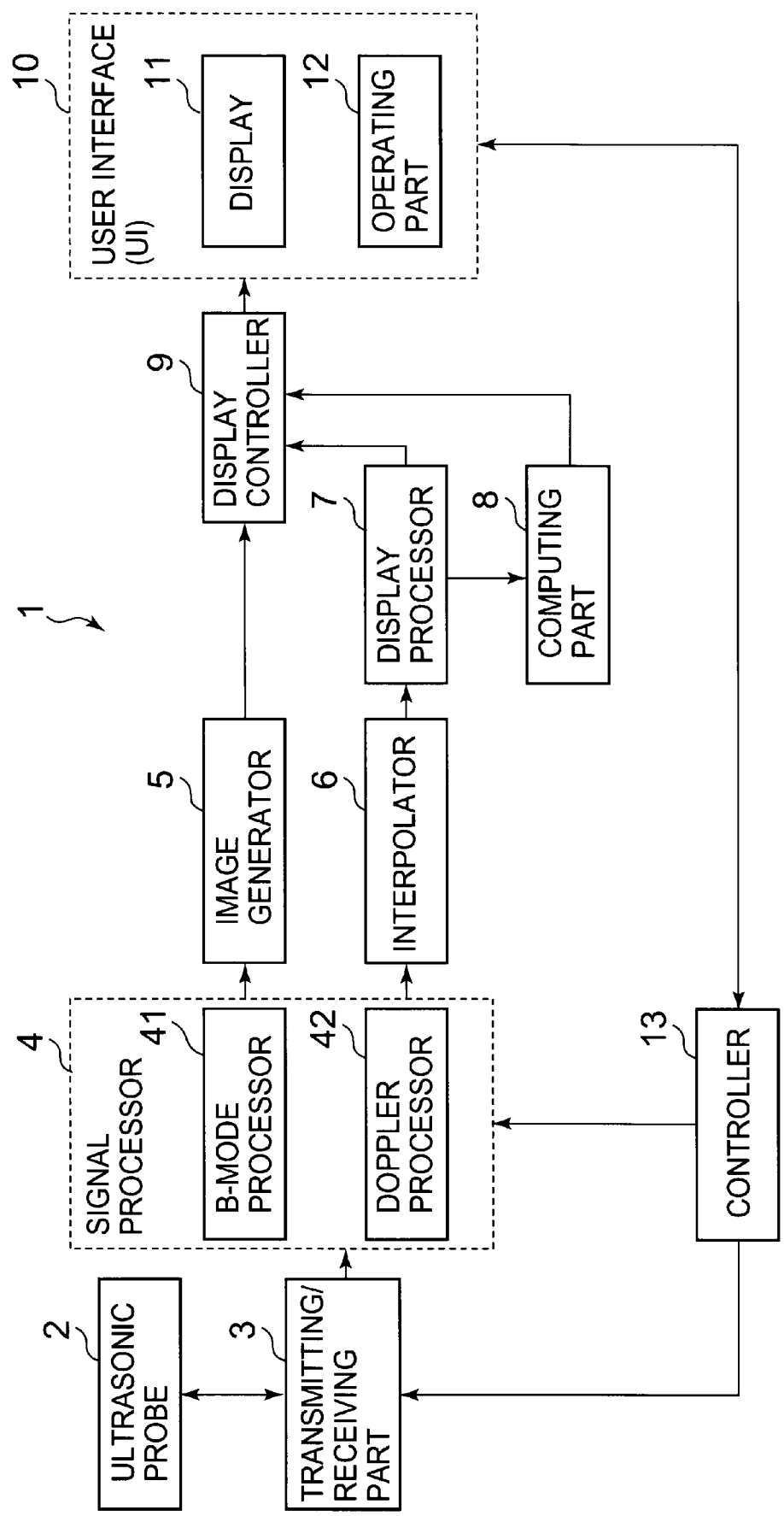
FIG. 1 is a block diagram showing an ultrasonic imaging apparatus according to an embodiment of the present invention.
Figure 2:
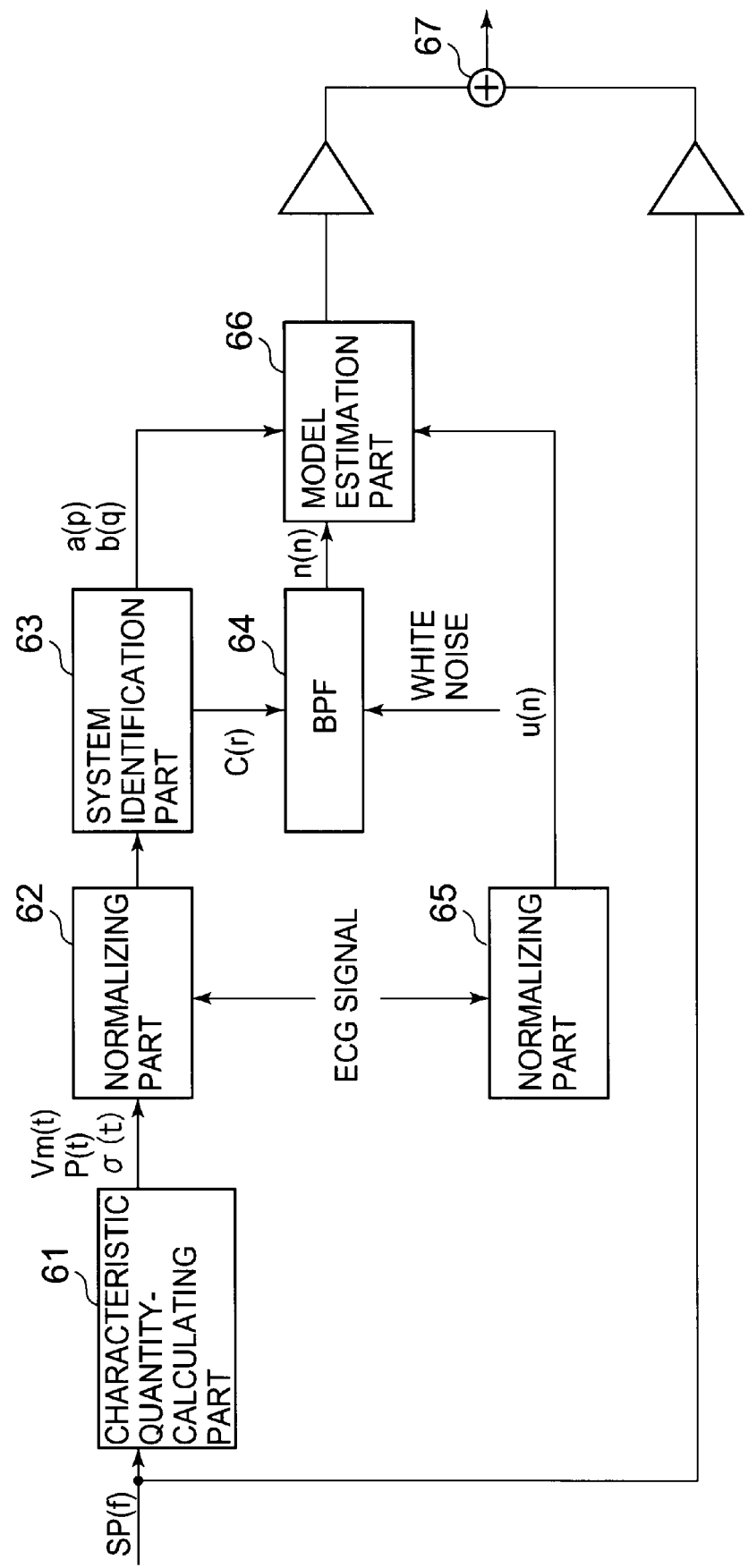
FIG. 2 is a block diagram showing an interpolator installed in the ultrasonic imaging apparatus according to an embodiment of the present invention.

FIG. 1 is a block diagram showing an ultrasonic imaging apparatus according to an embodiment of the present invention. FIG. 2 is a block diagram showing an interpolator installed in the ultrasonic imaging apparatus according to an embodiment of the present invention.

The ultrasonic imaging apparatus 1 according to the present embodiment comprises an ultrasonic probe 2, a transmitting/receiving part 3, a signal processor 4, an image generator 5, an interpolator 6, a display processor 7, a computing part 8, a display controller 9, a user interface (UI) 10, and a controller 13.

The ultrasonic imaging apparatus 1 transmits and receives ultrasound toward and from a subject to generate a Doppler spectrum image representing the flow rate of a moving body (blood flow) in the subject based on waves reflected from the subject. In the present embodiment, by way of example, a case is described in which the heart is the subject to be captured and a Doppler spectrum image of blood flow from the left ventricle in the systolic phase and a Doppler spectrum image of blood flow into the left ventricle into the diastolic phase are generated.

As for the ultrasonic probe 2, a 1D array probe with a plurality of ultrasonic transducers placed serially in a predetermined direction (scanning direction) is used. Alternatively, for the ultrasonic probe 2, a 2D array probe with a plurality of ultrasonic transducers placed in a two-dimensional manner may be used. By utilizing the 2D array probe, a three-dimensional region may be scanned with ultrasound, and volume data in the three-dimensional region may be acquired.

Furthermore, for the ultrasonic probe 2, a 1D array probe with a plurality of ultrasonic transducers placed serially in the scanning direction—a 1D array probe that can scan the three-dimensional region by mechanically oscillating the ultrasonic transducers in a direction perpendicular to the scanning direction-may be used.

The transmitting/receiving part 3 comprises a transmitting part and a receiving part. The transmitting/receiving part 3 supplies electrical signals to the ultrasonic probe 2 in order to generate ultrasound, and receives echo signals that have been received by the ultrasonic probe 2. The transmitting/receiving part 3 causes the ultrasonic probe 2 to transmit and receive ultrasound in accordance with a predetermined pulse repetition frequency (PRF).

The transmitting part of the transmitting/receiving part 3 comprises a clock generation circuit, a transmit delay circuit, and a pulsar circuit, which are not shown. The clock generation circuit issues clock signals that determines the transmission timing and transmission frequency of ultrasound signals. The transmission delay circuit causes a delay when transmitting the ultrasound in order to implement a transmission focus. The pulsar circuit has a number of pulsars corresponding to the number of individual channels per respective ultrasonic transducer. The pulsar circuit issues a drive pulse at the delayed transmission timing and supplies electrical signals to each ultrasonic transducer of the ultrasonic probe 2.

In addition, the receiving part of the transmitting/receiving part 3 comprises a preamplifier circuit, an A/D converter circuit, a receiving delay circuit, and an adder circuit, which are not shown. The preamplifier circuit amplifies echo signals output from each ultrasonic transducer of the ultrasonic probe 2 per receiving channel. The A/D converter circuit A/D converts the amplified echo signals. The receiving delay circuit provides the echo signals after A/D conversion with a delay time required to determine the reception of directional characteristics. The adder circuit adds the echo signals with the delay time provided. Due to that addition, a reflection component from a direction depending on the receiving directional characteristics is enhanced. In addition, the signals that have been added by this transmitting/receiving part 3 may be called "RF signals". The RF signals output from the transmitting/receiving part 3 is output to the signal processor 4.

The signal processor 4 comprises a B-mode processor 41 and a Doppler processor 42. Signals output from the transmitting/receiving part 3 are subject to a predetermined process by either processor.

The B-mode processor 41 visualizes information of echo amplification in order to generate B-mode ultrasonic raster data from the echo signals. Specifically, the B-mode processor 41 performs a band-pass filter process on the signals transmitted from the transmitting/receiving part 3, followed by detection of the envelope curve of the output signals. Then, the B-mode processor 41 visualizes information of echo amplification by applying a compression process with logarithmic conversion on the detected data.

The Doppler processor 42 generates blood flow information such as with the pulsed wave Doppler method (PW Doppler method).

According to the pulsed wave Doppler method, the Doppler shift frequency component at a certain depth may be detected because pulse waves are used. The velocity of blood flow at a particular site may be measured because it has this type of distance resolution. The Doppler processor 42 removes the Doppler shift frequency component by detecting received signals within the observation point having a particular size for signals transmitted from the transmitting/receiving part 3. Moreover, the Doppler processor 42 generates the Doppler frequency distribution representing the blood flow velocity at the observation point having a predetermined size by FFT processing.

The Doppler processor 42 comprises a quadrature detection part, a range gate (RG) processor, a wall filter, and a FFT computing part, which are not shown.

The quadrature detection part comprises a digital mixer and a low-pass filter (LPF) corresponding to an actual component and an imaginary component, respectively, and performs the quadrature detection of RF signals. Then, the quadrature detection part outputs a digital amount of IQ signals that have undergone quadrature detection.

With this detection, the Doppler signals (actual and imaginary components: IQ signals) of the baseband are extracted from RF signals.

The range gate (RG) processor obtains Doppler signals consisting of Doppler shift frequency components only by receiving IQ signals output from the quadrature detection part and removing high frequency components of these IQ signals. Then, the range gate processor extracts Doppler signals at a desired depth in the subjects among the Doppler signals consisting of only Doppler shift frequency components.

The wall filter removes unnecessary low frequency Doppler signals representing the blood vessel wall and heart wall having relatively slow movement from Doppler signals (IQ signals) at a site designated at the range gate processor. Then, the wall filter extract Doppler signals (IQ signals) of the blood flow to be detected.

The FFT computing part analyzes the frequency of the Doppler signals (IQ signals) that have been extracted using the wall filter, thereby obtaining Doppler spectrum signals, which are the result of the analysis thereof.

The display controller 9 causes Doppler spectrum signals obtained by the FFT computing part to be displayed on the display 11.

Specifically, the display controller 9 causes the Doppler spectrum image with frequency f (velocity v) on the vertical line and time t on the horizontal line represented to be displayed on the display 11.

The image generator 5 generates ultrasonic image data based on data that has been processed by the B-mode processor 41. For example, the image generator 5 comprises a DSC (Digital Scan Converter) and converts the data that has been processed by the B-mode processor 41 into image data represented using the orthogonal coordinate system in order to obtain an image represented using the orthogonal coordinate system (scan conversion process). For example, the image generator 5 generates a cross-sectional image data as two-dimensional information based on B-mode ultrasonic raster data and outputs that cross-sectional image data to the display controller 9. The display controller 9 causes a cross-sectional image based on that cross-sectional image data to be displayed on the display 11.

In addition, after carrying out volume scanning by the ultrasonic probe 2 and the transmitting/receiving part 3 to acquire volume data, the image generator 5 generates three-dimensional image data sterically representing the tissue form of a subject by subjecting the volume data to volume rendering. In addition, the image generator 5 may generate image data on an arbitrary section (MPR image data) by subjecting the volume data to MPR processing (Multi Planar Reconstruction). The image generator 5 outputs ultrasonic image data such as three-dimensional image data and MPR image data to the display controller 9. The display controller 9 causes three-dimensional images based on three-dimensional data and MPR images based on MPR image data to be displayed on the display 11.

Setting Observation Points

With an ultrasonic image such as a cross-sectional image or a three-dimensional image displayed on the display 11, the operator designates a position from which one would like to acquire blood flow information on the ultrasonic image by means of an operating part 12.

Specifically, the position from which one would like to acquire blood flow information is designated by setting an observation point (range gate) on the ultrasonic image. The observation point (range gate) has a predetermined size. The range designated by this observation point (range gate) is the range for the Doppler scan, and blood flow information at that observation point is acquired.

In the present embodiment, blood flow information of a plurality of sites are acquired by setting a plurality of observation points (range gates). For example, measurement of the left ventricular inflow or left ventricular outflow is suitable for evaluating the cardiac function.

Therefore, the site where the left ventricular inflow occurs and the site where the left ventricular outflow occurs are designated using observation points (range gates). The left ventricular inflow occurs at the mitral valve tip and the left ventricular outflow occurs at the aortic valve tip. Therefore, the left ventricular inflow and left ventricular outflow can be measured by displaying an ultrasonic image in which the mitral valve tip and aortic valve tip are represented on the display 11 and setting the observation points (range gates) at the position of the mitral valve tip and the position of the aortic valve tip represented on that ultrasonic image. Specific examples of setting the observation points (range gates) are described as follows.

First Example of Setting Observation Points

Figure 4:
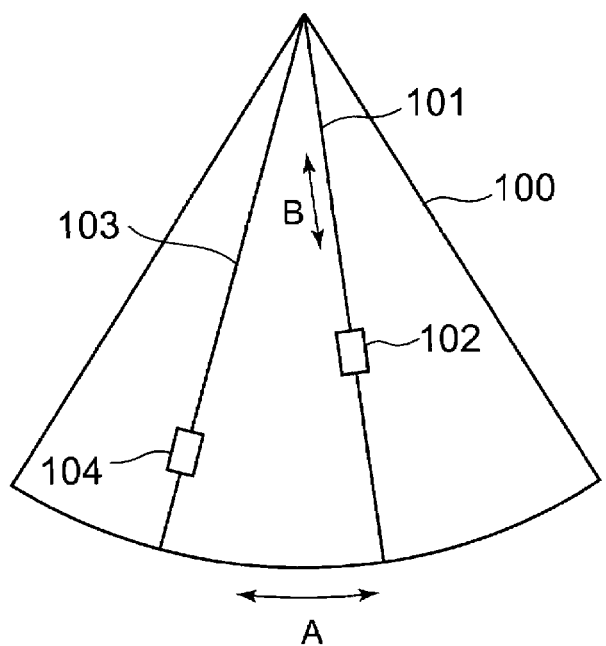
FIG. 4 is a diagram for describing the first example of setting an observation point, the diagram illustratively showing a cross-sectional image.

First, the first example of setting observation points is described with reference to FIG. 4. FIG. 4 is a diagram for describing the first example of setting an observation point, the diagram illustratively showing a cross-sectional image. In the first example of setting observation points, a cross-sectional image of the subject is acquired and displayed on the display 11 to set observation points (range gates) at the position of the mitral valve tip and the position of the aortic valve tip represented on that cross-sectional image.

First, by scanning a cross-section in the subject via ultrasonic wave with the ultrasonic probe 2 and the transmitting/receiving part 3, received signals for that cross-section are acquired. The B-mode processor 41 generates B-mode ultrasonic raster data for that cross-section based on these received signals. The image generator 5 generates cross-sectional image data representing the tissue for that cross-section based on the B-mode ultrasonic raster data. As shown in FIG. 4, the display controller 9 causes a cross-sectional image 100 based on that cross-sectional image data to be displayed on the display 11. Scanning is performed with the ultrasonic probe 2 and the transmitting/receiving part 3 while changing the position and angle of the ultrasonic probe 2 on the subject so that the mitral valve tip and the aortic valve tip are represented in the cross-sectional image 100.

The operator designates the position of the mitral valve tip and the position of the aortic valve tip represented in the cross-sectional image 100 by means of the operating part 12 while observing the cross-sectional image 100 displayed on the display 11. For example, the display controller 9 causes observation point 102 and observation point 104, which can move on the cross-sectional image 100, to be displayed on the display 11. Observation point 102 and observation point 104 each have predetermined sizes. With observation point 102 and observation point 104, each range of the determined sizes may be designated. In addition, the operator may change the sizes of observation point 102 and observation point 104 by means of the operating part 12. The operator designates the position of the mitral valve tip and the position of the aortic valve tip with observation point 102 and observation point 104, respectively. The display controller 9 causes the linear sample line 101 and sample line 103 to overlap on the cross-sectional image 100, the linear sample line 101 showing the direction of transmission and reception of ultrasound, and causes it to be displayed on the display 11. The operator may move sample line 101 and sample line 103 in the scanning direction (direction of arrow A) by means of the operating part 12. The operator may move observation point 102 on sample line 101 in the direction of transmission and reception of ultrasound (direction of arrow B) by means of the operating part 12. Similarly, the operator may move observation point 104 on sample line 103 in the direction of transmission and reception of ultrasound by means of the operating part 12.

For example, the operator moves sample line 101 to the position of the mitral valve tip by means of the operating part 12 and moreover moves observation point 102 in the direction of transmission and reception (direction of arrow B), thereby designating the position of the mitral valve tip with observation point 102. Similarly, the operator moves sample line 103 to the position of the aortic valve tip by means of the operating part 12 and moreover moves observation point 104 in the direction of transmission and reception (direction of arrow B), thereby designating the position of the aortic valve tip with observation point 104. In this way, when a site from which one would like to obtain blood flow information is designated with the observation point (range gate), coordinate information showing the position of the observation point on the cross-sectional image 100 is output from the user interface (UI) 10 to the controller 13.

In addition, the operations of observation point 102 and observation point 104 may be switched with a toggle action. For example, a changeover switch is installed in the operating part 12, and in the default state, the display controller 9 fixes observation point 104 on the cross-sectional image and causes it to be displayed on the display 11. In this state, the operator can operate observation point 1 02 by means of the operating part 12. Then, the operator presses the changeover switch, thereby causing the display controller 9 to fix observation point 102 on the cross-sectional image and be displayed, and the operator can operate observation point 104 by means of the operating part 12.

Angle Correction

Moreover, the angle formed by the blood flow at a site where observation point 102 has been set and the direction of transmission and reception of the ultrasonic beam is obtained on the cross-sectional image 100. Similarly, an angle formed by the blood flow at a site where observation point 104 has been set and the direction of transmission and reception of the ultrasonic beam is obtained on the cross-sectional image 100. For example, the display controller 9 causes a linear angle marker for designating the direction of blood flow to overlap the cross-sectional image 100 and be displayed on the display 11. The operator orients the angle marker toward the direction of the blood flow by means of the operating part 12. Specifically, the operator orients the angle marker by means of the operating part 12 toward the direction of the blood flow at a site where observation point 102 has been set. Similarly, the operator orients the angle marker by means of the operating part 12 toward the direction of the blood flow at a site where observation point 104 has been set. The orientation of this angle marker indicates the direction of the blood flow. The controller 13 obtains an angle between the direction of the transmission and reception of ultrasonic beam at the site where observation point 102 has been set and the orientation of the angle marker, and outputs that angle to the Doppler processor 42. Similarly, the controller 13 obtains the angle between the direction of transmission and reception of the ultrasonic beam at the site where observation point 104 has been set and the orientation of the angle marker and outputs that angle to the Doppler processor 42. The Doppler processor 42 obtains the blood flow velocity at observation point 102 and observation point 104 using each angle.

When controller 13 receives coordinate information at each observation point (range gate) that has been designated by the operator via the user interface (UI) 10, coordinate information at each observation point is output to the transmitting/receiving part 3 and the Doppler processor 42 of the signal processor 4.

The transmitting/receiving part 3 deflects an ultrasonic beam with the ultrasonic probe 2 in accordance with the coordinate information at the observation point (range gate) that has been set by the controller 13. Then, the transmitting/receiving part 3 obtains Doppler information (blood flow information) at each observation point by Doppler scanning via the pulsed wave Doppler method. Then, the Doppler processor 42 obtains the blood flow velocity at each observation point in accordance with the observation point (range gate) that has been set by the controller 13. In the abovementioned example, the position of the mitral valve tip is designated by observation point 102 and the position of the aortic valve tip is designated by observation point 104. Therefore, the transmitting/receiving part 3 obtains Doppler information of the mitral valve tip and Doppler information of aortic valve tip. The Doppler processor 42 acquires the blood flow velocity at the mitral valve tip designated by observation point 102, and the blood flow velocity at the aortic valve tip designated by observation point 1 04. The Doppler processor 42 obtains the blood flow velocity using an angle consisting of the blood flow and the direction of transmission and reception of the ultrasonic.

Segment Scanning

Figure 5:
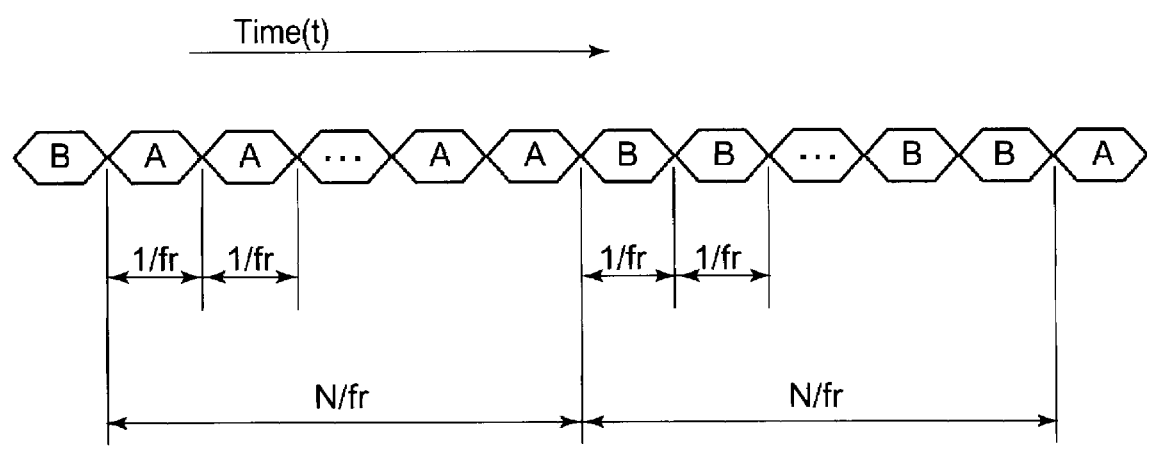
FIG. 5 is a diagram showing a sequence of scanning that the ultrasonic imaging apparatus carries out according to an embodiment of the present invention.

In the present embodiment, the transmitting/receiving part 3 performs segment scanning under the control of the controller 13, thereby acquiring Doppler information at each position designated by observation point 102 and observation point 104. Segment scanning carried out in the present embodiment is described with reference to FIG. 5. FIG. 5 is a diagram showing the sequence of scanning that the ultrasonic imaging apparatus carries out according to the present embodiment. In FIG. 5, the horizontal axis represents time (t).

The controller 13 has a memory device that is not shown, and scanning conditions are pre-memorized in that memory device. In the present embodiment, the transmitting/receiving part 3 serially transmits and receives ultrasound toward and from the same observation point at a plurality of times under the control of the controller 13 and subsequently serially transmits and receives ultrasound toward and from another observation point at a plurality of times. Then, the transmitting/receiving part 3 serially transmits and receives ultrasound toward and from the same observation point at a plurality of times, and periodically transmits and receives ultrasound toward and from each observation point. For example, when two observation points are designated, the transmitting/receiving part 3 serially transmits and receives ultrasound toward and from one observation point at a plurality of times under the control of the controller 13, and subsequently, it serially transmits and receives ultrasound toward and from the other observation point at a plurality of times. The transmitting/receiving part 3 continues to serially transmit and receive ultrasound toward and from each observation point in an alternate manner at a plurality of times. The scanning conditions include the number of times for serially transmitting and receiving ultrasound toward and from the same observation point, and the pulse repetition frequency (PRF). The operator may arbitrarily change that number of times by means of the operating part 12.

For example, when two sites are designated by observation point 102 and observation point 104, the transmitting/receiving part 3 serially transmits and receives ultrasound toward and from observation point A (observation point 102) under the control of the controller 13 at N times, as shown in FIG. 5, and subsequently, it serially transmits and receives ultrasound toward and from observation point B (observation point 104) at N times. The transmitting/receiving part 3 continues to variously transmit and receive ultrasound alternately toward and from observation point A (observation point 102) and observation point B (observation point 104) at N times. In addition, in the example shown in FIG. 5, the transmitting/receiving part 3 is transmitting and receiving ultrasound toward and from each observation point in accordance with the pulse repetition frequency fr.

The transmitting/receiving part 3 outputs, to the Doppler processor 42, Doppler information at each observation point that has been acquired via Doppler scanning. The Doppler processor 42 generates a series of Doppler spectrum images at each observation point by analyzing the frequency of the Doppler information that has been output from the transmitting/receiving part 3 under the control of the controller 13. In the present embodiment, the Doppler processor 42 generates a series of Doppler spectrum images at observation point 102 (observation point A) and a Doppler spectrum image at observation point 104 (observation point B) under the control of the controller 13.

Then, the display controller 9 causes the Doppler spectrum image at observation point 102 and the Doppler spectrum image at observation point 104 to be displayed on the display 12.

In addition, one example of the "Doppler scanner" in the present invention comprises an ultrasonic probe 2, a transmitting/receiving part 3 and a controller 13. Moreover, the Doppler processor 42 corresponds to one example of the "processor" according to the present invention. Moreover, one example of the "image-acquiring part" according to the present invention comprises an ultrasonic probe 2, a transmitting/receiving part 3, a B-mode processor 41, and an image generator 5.

Figure 6:
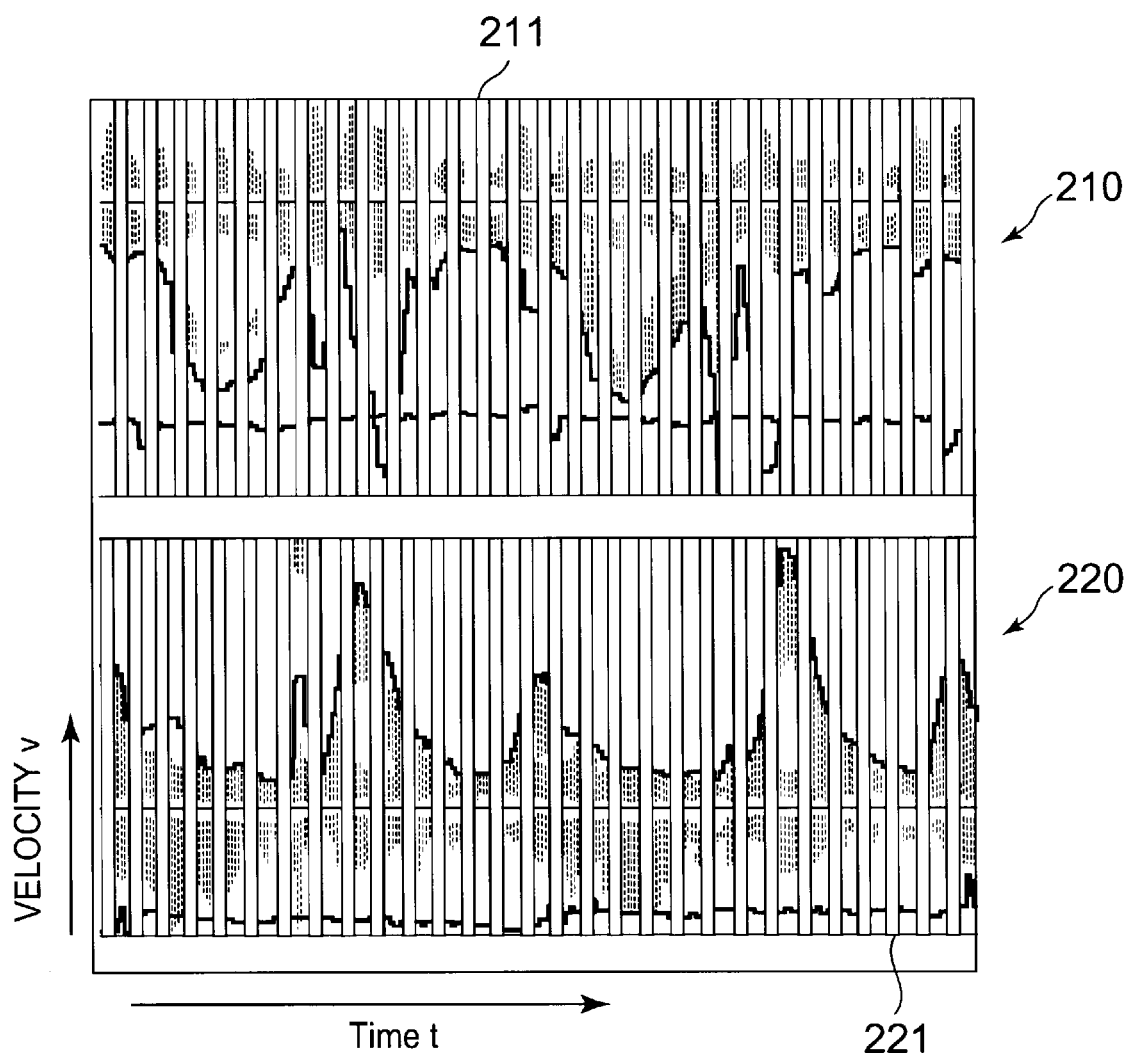
FIG. 6 is a diagram showing one example of a Doppler spectrum image acquired by the ultrasonic imaging apparatus according to an embodiment of the present invention.

Now, a Doppler spectrum image acquired via segment scanning according to the present embodiment is described with reference to FIG. 6. FIG. 6 is a diagram showing one example of a Doppler spectrum image acquired by the ultrasonic imaging apparatus according to an embodiment of the present invention. In FIG. 6, the horizontal axis represents time (t) and the vertical axis represents blood flow velocity (v).

A Doppler spectrum image 210 represents the blood flow velocity at observation point 104. Because observation point 104 has been set to the position of the aortic valve tip, the Doppler spectrum image 210 represents the velocity of the left ventricular outflow at the aortic valve tip. On the other hand, a Doppler spectrum image 220 represents the blood flow velocity at observation point 102. Because observation point 102 has been set to the position of the mitral valve tip, the Doppler spectrum image 220 represents the velocity of the left ventricular inflow at the mitral valve tip.

As described above, according to the ultrasonic imaging apparatus I of the present embodiment, by alternately transmitting and receiving ultrasound toward and from each observation point at a plurality of times (N times), a Doppler spectrum image at each observation point can be acquired without reducing the Doppler velocity range (fr). In addition, because the velocity of the left ventricular inflow and the velocity of the left ventricular outflow are each obtained from the same heartbeat, indices such as the left ventricular ejection fraction (E/F) are less apt to be unstable even when the heart rate varies. Moreover, it is possible to attempt to improve reproducibility of the indices.

Comparison with the Prior Art

Figure 16:
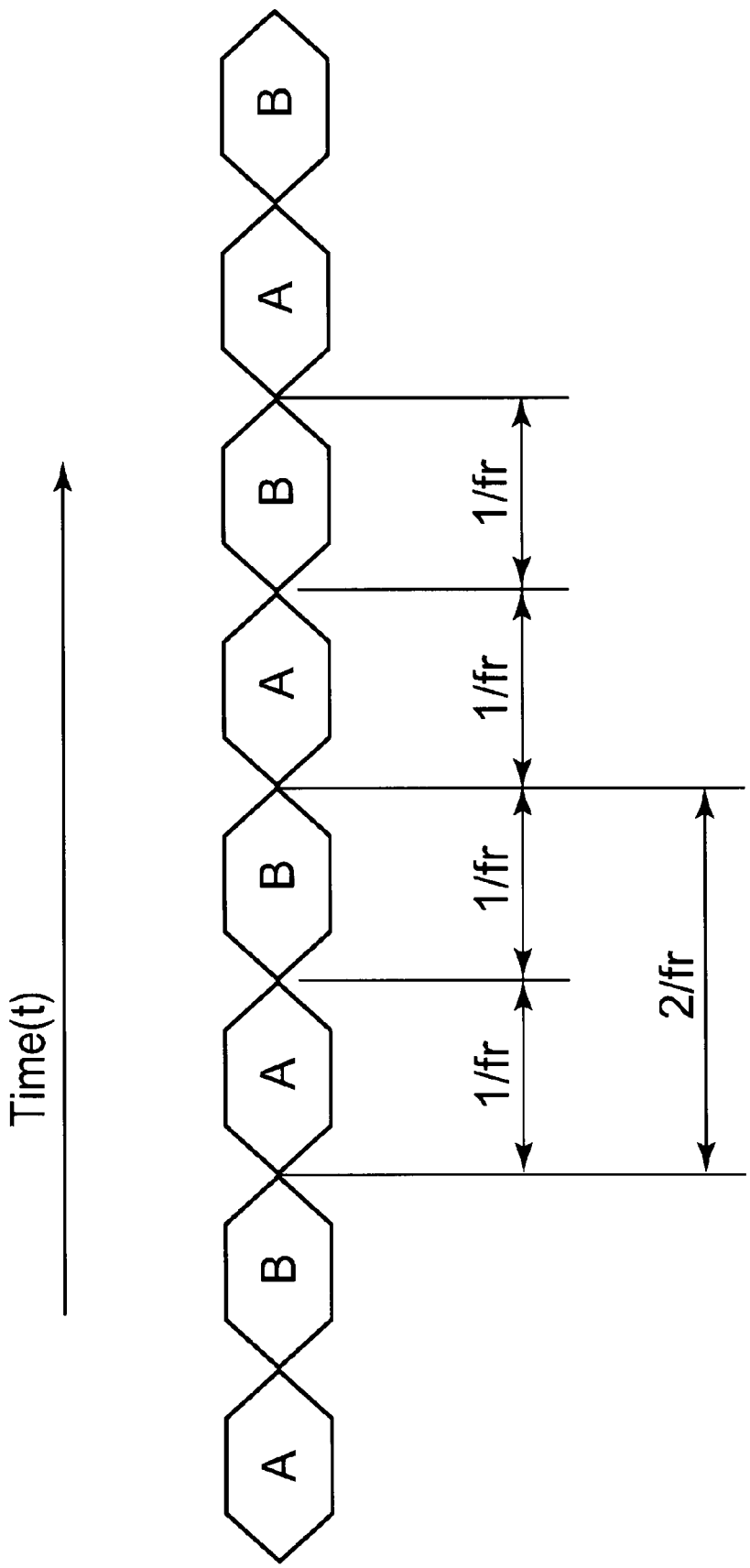
FIG. 16 is a diagram showing a sequence of the scanning according to the prior art.

Now, referring to FIG. 5 and FIG. 16, the method of transmitting and receiving ultrasound according to the present embodiment and the transmitting and receiving method according to the prior art will be compared. FIG. 16 is a diagram showing the sequence of scanning according to the prior art. In FIG. 16, the horizontal axis represents time (t).

For example, when Doppler spectrum images at two observation points are acquired, in the prior art, as shown in FIG. 16, by alternately transmitting and receiving ultrasound toward and from observation point A and observation point B once each, a Doppler spectrum image at observation point A and a Doppler spectrum image at observation point B were acquired. According to this transmitting and receiving method according to the prior art, because the pulse repetition frequency PRF becomes half, the Doppler velocity range accordingly becomes half. As a result, there is a problem in which the folding phenomenon occurs in the Doppler spectrum image.

Conversely, according to the ultrasonic image apparatus 1 in the present embodiment, by alternately transmitting and receiving ultrasound toward and from observation point A and observation point B variously at N times, a Doppler spectrum image at observation point A and a Doppler spectrum image at observation point B can be acquired without reducing the Doppler velocity range.

However, according to the ultrasonic image apparatus 1 in the present embodiment, while ultrasound is being serially transmitted toward and received from a certain observation point at a plurality of times, no ultrasound is being transmitted toward or received from other observation points. Therefore, there is a problem in which data is periodically missing in the Doppler spectrum image at each observation point. For example, at a time when ultrasound is being transmitted toward and received from observation point 102 (observation point A), no blood flow information at observation point 104 (observation point B) is acquired. Similarly, at a time when ultrasound is being transmitted toward and received from observation point 104 (observation point B), no blood flow information at observation point 102 (observation point A) is acquired. Accordingly, as shown in FIG. 6, a periodic data-missing part 211 occurs in the Doppler spectrum image 210 at observation point 104. Furthermore, a periodic data-missing part 221 occurs in the Doppler spectrum image 220 at observation point 102.

Then, the longer the time interval when ultrasound is serially transmitted toward and received from each observation point, the longer will be the time when no blood flow information is acquired at each observation point. Thus, in the present embodiment, by interpolating periodically missing data, a temporary consecutive Doppler spectrum image is generated. The interpolator 6 performs this interpolation. The interpolator 6 will be described later.

It is preferable for the number of times N for serially transmitting and receiving ultrasound toward and from the same observation point to be determined in accordance with the pulse repetition frequency PRF and time duration for serially transmitting and receiving ultrasound toward and from the same observation point.

For example, it is preferable to determine the number of times N based on the pulse repetition frequency PRF so that the time duration for serially scanning the same observation point would be within 100 ms. By way of example, when the pulse repetition frequency PRF is 4 kHz and the time duration for serially transmitting and receiving ultrasound toward and from the same observation point is 100 ms, the number of times N will be up to 400. That is, when the pulse repetition frequency PRF is 4 kHz, it is preferable to serially transmit and receive ultrasound toward and from the same observation point ≤400 times. In addition, it is preferable to set the time duration for serially transmitting and receiving ultrasound toward and from the same observation point to 100 ms or less. While ultrasound is being serially transmitted toward and received from the same observation point, data at the other observation points will be missing. In order to obtain that missing data by interpolating via the interpolator 6, it is preferable to be 100 ms or less. The number of times N depends on the pulse repetition frequency PRF, but in order to set the time duration for serially transmitting and receiving ultrasound toward and from the same observation point to 100 ms or less, it is preferable for the number of times N to be between several dozen and several hundreds.

Interpolation

Figure 8B:
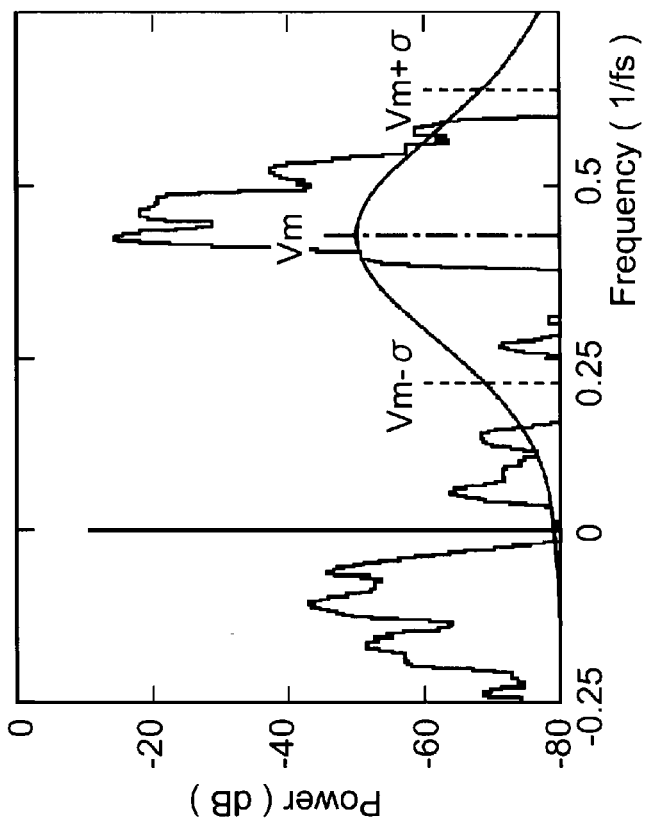
FIG. 8B is a diagram showing spectral dispersion σ and the power spectrum.
Figure 8A:
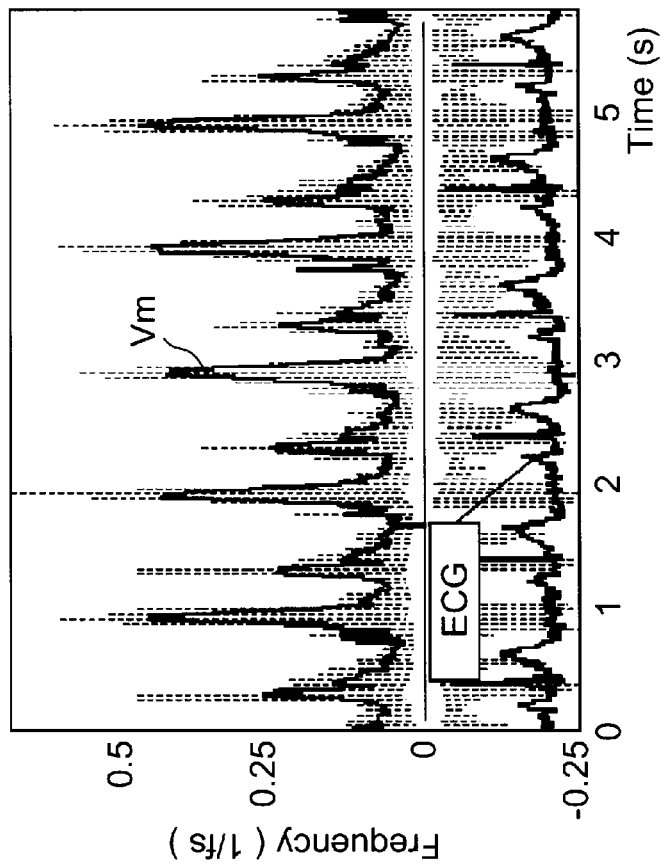
FIG. 8A is a diagram of the average flow rate Vm.

Next, interpolation by the interpolator 6 will be described with reference to FIG. 2, FIG. 7, FIG. 8A, FIG. 8B, and FIG. 9. FIG. 7 is a diagram for describing the process of interpolating a part with data missing in the Doppler spectrum. In FIG. 7, the horizontal axis represents time (t). FIG. 8A is a diagram showing the average flow rate Vm. FIG. 8B is a diagram showing spectral dispersion σ and the power spectrum.

As described above, in the Doppler spectrum image 220 at observation point 102 (observation point A), periodic data-missing parts 221 occur. Furthermore, in the Doppler spectrum image 210 at observation point 104 (observation point B), periodic data-missing parts 211 occur. Therefore, in the present embodiment, by interpolating periodically missing data, consecutive Doppler spectrum image data is generated. In the present embodiment, using ECG (electrocardiogram) signals of the subject, by system identification with a parametric model such as the ARMAX model (Auto Regressive and Moving Average Exogenous model), the spectrum of the part with data missing is estimated.

For example, as shown in FIG. 7, at a time when ultrasound is being transmitted toward and received from observation point B (observation point 104), in a Doppler spectrum image at observation point A (observation point 102), a gap (B) resulting from the transmission and reception occurs. This gap (B) corresponds to the data missing part 221 in the Doppler spectrum image 220. In the present embodiment, the interpolator 6 obtains a characteristic quantity based on Doppler spectrum image data at observation point A that has been obtained at a point just before the time when the data-missing part (gap B) occurs. Then, the interpolator 6 calculates forward predictive coefficient sequences a (k1), b (k2), or residual bandwidth BW coefficients c (k3) using the quantity of characteristics and ECG signals (forward estimation). For example, the interpolator 6 obtains the average flow rate Vm, Doppler spectral dispersion σ, and Doppler spectral total power TP as the quantity of characteristics. Then, the interpolator 6 predicts Doppler spectrum image data (estimated data) in the missing part (gap B) using these coefficients obtained based on the Doppler spectrum image data that has been obtained at a point just before the missing part (gap B) occurs. In addition, in order to improve the link between the estimated data at the missing part (gap B) and the Doppler spectrum image data (actual data) at observation point A that has actually been obtained, a blending (synthesis) is performed by overlapping the actual data and the estimated data. For blending, for example, by weighting the actual data and the estimated data for the addition, the link between the actual data and the estimated data is improved. In addition, if the time required to output the estimated data is short, the estimation may be performed also from the reverse direction (backward) of time (backward estimation). In this case, by blending the estimated data that has been obtained with forward estimation and the estimated data that has been obtained with backward estimation, the spectrum at the gap B is obtained.

The specific process performed by the interpolator 6 will be described with reference to FIG. 2. The interpolator 6 comprises a characteristic quantity-calculating part 61, a normalizing part 62, a system identification part 63, a BPF 64, a normalizing part 65, a model estimation part 66, and an adding part 67.

In the present embodiment, the electrocardiographic waveform (ECG signals) of the subject is obtained by means of an electrocardiograph installed on the exterior of the ultrasonic imaging apparatus 1, and output to the ultrasonic imaging apparatus 1. The controller 13 receives ECG signals that have been output from the electrocardiograph and outputs those ECG signals to the interpolator 6.

The characteristic quantity-calculating part 61 receives a Doppler spectrum image SP (f) that has been output from the Doppler processor 42 to obtain the time change of the power spectrum. Then, the characteristic quantity-calculating part 61 obtains the quantity of characteristics at a point just before a time when the data-missing part (gap) occurs. The characteristic quantity-calculating part 61 obtains, for example, the average flow rate Vm, spectral dispersion σ, and spectral total power TP as the quantity of characteristics. In order to interpolate data missing at observation point A (observation point 102), the characteristic quantity-calculating part 61 obtains the average flow rate Vm, dispersion σ, and total power TP at a point just before a time when the data missing part (gap B) occurs based on the Doppler spectrum image data at observation point A. In addition, in order to interpolate data missing at observation point B (observation point 104), the characteristic quantity-calculating part 61 obtains the average flow rate Vm, dispersion σ, and total power TP at a point just before a time when the data missing part (gap A) occurs based on the Doppler spectrum image data at observation point B. In the following description, a case in which data missing in the Doppler spectrum image at observation point A is interpolated will be described.

Expressions for obtaining the average flow rate Vm, spectral dispersion σ, and total power TP are shown as follows.

$$Vm = \left(\frac{C}{2}\right) * \frac{\sum_{k=0}^{95} f_k * P(f_k)}{\sum_{k=0}^{95} P(f_k)} \quad \text{Expression (1)}$$

$$\sigma = \sqrt{\frac{\sum_{k=0}^{95}\left(f_k - \frac{2*Vm}{c}\right)^2}{96}} \quad \text{Expression (2)}$$

$$TP = \sum_{k=0}^{95} P(f_k) \quad \text{Expression (3)}$$

Expression (1) is an expression for obtaining the average flow rate Vm. Expression (2) is an expression for obtaining the dispersion σ.

Expression (3) is an expression for obtaining the total power TP.

In Expression (1) through Expression (3), P (f) represents power spectrum, f is a frequency normalized with the FFT sampling frequency fs, and C represents the sound velocity. In the present embodiment, because the Doppler spectrum image SP (f) of the left ventricular inflow is an input, calculation is performed using the positive velocity component only.

By way of example, the point number k of the frequency in FFT was k=0 to 95.

In addition, the average flow rate Vm, dispersion σ, and power spectrum are shown in FIG. 8A and FIG. 8B. In the graph shown in FIG. 8A, the horizontal axis represents time (t), and the vertical axis represents a frequency (f) normalized with FFT sampling frequency fs.

The graph shown in FIG. 8A represents the average flow rate Vm at each time. In addition, in the graph shown in FIG. 8B, the horizontal axis represents a frequency (f) normalized with FFT sampling frequency fs, and the vertical axis represents power. The graph shown in FIG. 8B represents the average flow rate Vm, dispersion σ and power [dB] at each time.

The characteristic quantity-calculating part 61 obtains Vm (n), σ (n), and TP (n) at each time phase based on the Doppler spectrum image data at observation point A and outputs them to the normalizing part 62. The normalizing part 62 normalizes Vm (n), σ (n), and TP (n) at each time phase at observation point A. Moreover, the normalizing part 62 receives ECG signals as deterministic external input from the controller 13 to normalize the ECG signals. Then, the normalizing part 62 outputs the normalized Vm (n), σ (n), TP (n), and ECG signals to the system identification part 63.

The system identification part 63 obtains the forward predictive coefficient sequences $a_k$, $b_k$, and $c_k$ of the ARMAX model by identifying the system using Vm (n), σ (n), and TP (n), which are the quantity of characteristics at observation point A, and ECG signals, which are deterministic external input. In system identification with a parametric model such as the ARMAX model, with the heartbeat period of the blood flow as criteria, coefficient sequence data that has undergone regression in the model representing a variation in the Doppler spectrum.

Figure 3:
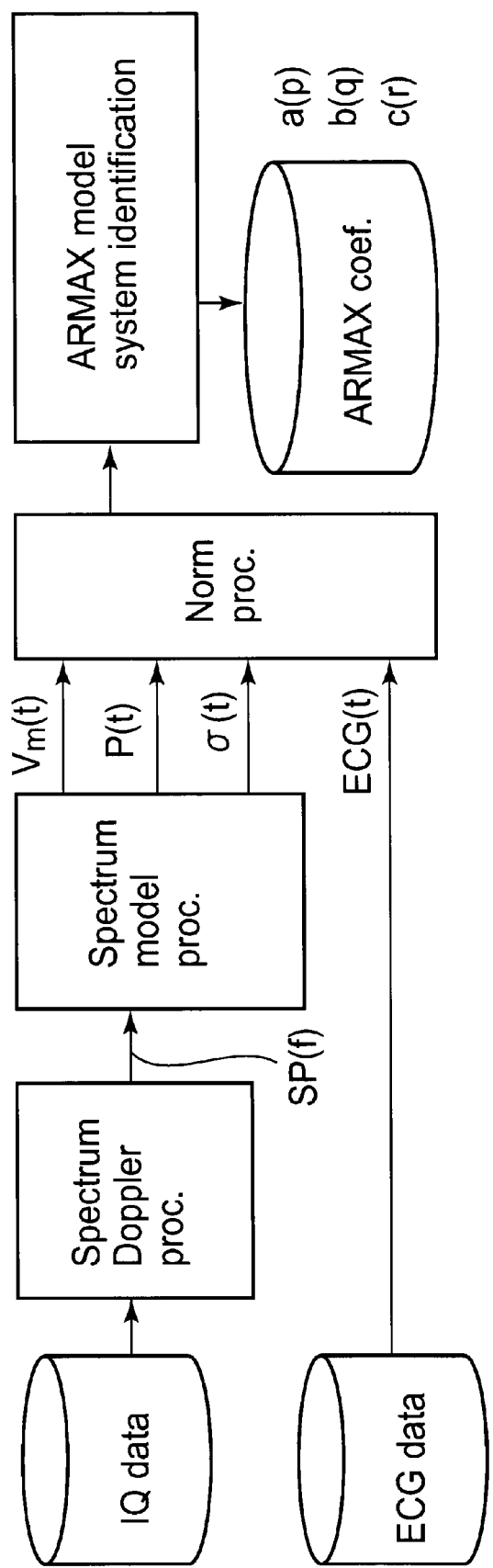
FIG. 3 is one example of a system identification part according to an embodiment of the present invention.

Now, the system identification part 63 will be specifically described with reference to FIG. 3. FIG. 3 is a block diagram showing a detailed example of the system identification part according to an embodiment of the present invention. FIG. 3 shows system identification based on the Doppler spectrum image SP (f) of the left ventricular inflow and ECG signals. Illustratively showing the average flow rate Vm and dispersion σ, by way of example, a spectrum Doppler processor has modeled the spectrum near 2 seconds of time in the spectrum image shown in FIG. 8A. The system identification via the ARMAX model calculates coefficient sequence data regressed to the model representing spectral variation with the heart rate of the blood flow as criteria.

The BPF 64 receives coefficient $c_k$ of the ARMAX model and white noise, with band-limitation of the noise source, outputting the output value n (n) to the model-estimation part 66. In addition, the normalizing part 65 receives ECG signals as deterministic external input from the controller 13 to normalize and output those ECG signals to the model-estimation part 66.

The model estimation part 66 estimates the missing spectrum by performing spectral estimation by means of the ARMAX model. In the present embodiment, the model-estimation part 66 performs forward estimation only, and adds definite ECG signals other than noise. Here, the predictive output of the ARMAX model is shown in Expression (4).

$$y(n) = \sum_{k=1}^{P} a_k * y(n-k) + \sum_{k=1}^{q} b_k * u(n-k) + \sum_{k=1}^{r} c_k * n(n-k)$$

$$\text{where } y(n) = \begin{bmatrix} Vm(n) \\ \sigma(n) \\ TP(n) \end{bmatrix}$$

Expression (4)

In Expression (4), $a_k$, $b_k$, and $c_k$ are coefficients of the ARMAX model, and u (n) is a waveform in which the time axis and amplitude of the ECG signals have been normalized. In addition, in Expression (4), the quantity of characteristics of the Doppler spectrum image is represented by a determinant.

The adding part 67 generates consecutive Doppler spectrum image data at the observation point A by combining estimated data that has been estimated via the ARMAX model and actual data representing the Doppler spectrum image at observation point A that has actually been obtained. In this case, the adding part 67 generates blend data by blending the actual data and the estimated data at the border of the actual data and the estimated data shown in FIG. 7. Then, the interpolator 6 outputs, to the display processor 7, the Doppler spectrum image data that has undergone interpolation. Furthermore, the interpolator 6 interpolates the Doppler spectrum image data at observation point B via the same process.

In addition, the interpolator 6 may receive the Doppler spectrum image data from the Doppler processor 42 in order to interpolate in the time direction based on the data before and after the part with data missing, obtaining data in a missing part. For example, the interpolator 6 obtains data in the missing part 211 by interpolation in the time direction based on the data before and after the data-missing part 211 in the Doppler spectrum image 210.

Figure 9:
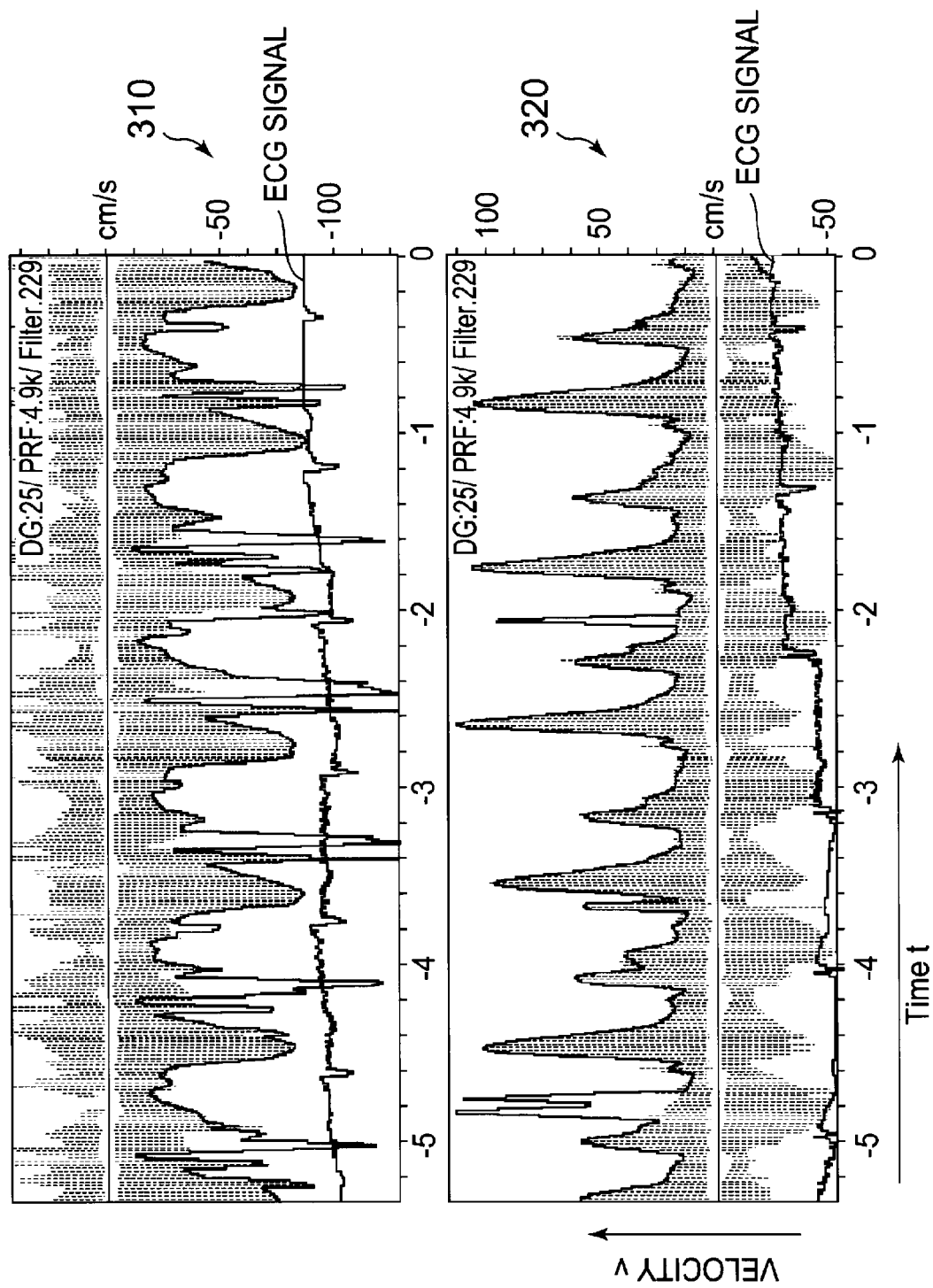
FIG. 9 is a diagram showing one example of a Doppler spectrum image acquired by the ultrasonic imaging apparatus according to an embodiment of the present invention.

The Doppler spectrum image generated via interpolation by the interpolator 6 is shown in FIG. 9. FIG. 9 is a diagram showing one example of a Doppler spectrum image acquired by the ultrasonic image apparatus according to an embodiment of the present invention. In FIG. 9, the horizontal axis represents time (t) and the vertical axis represents the blood flow velocity (v). The display controller 9 causes a Doppler spectrum image interpolated by the interpolator 6 to be displayed on the display 11.

A Doppler spectrum image 310 represents the velocity of the blood flow at observation point 104. Because observation point 104 has been set at the position of the aortic valve tip, the Doppler spectrum image 310 represents the velocity of the left ventricular outflow at the aortic valve tip. On the other hand, a Doppler spectrum image 320 represents the velocity of the blood flow at observation point 102.

Because observation point 102 has been set at the position of the mitral valve tip, the Doppler spectrum image 320 represents the velocity of the left ventricular inflow at the mitral valve tip.

The display controller 9, such as shown in FIG. 9, causes the Doppler spectrum image 3 1 0 and the Doppler spectrum image 320 to be simultaneously displayed on the display I1. In the example shown in FIG. 9, the display controller 9 causes the Doppler spectrum image 310 and the Doppler spectrum image 320 to be displayed side by side on the display 11.

Because periodically missing data in each Doppler spectrum image is interpolated via interpolation by the interpolator 6, consecutive Doppler spectrum images 310, 320 as shown in FIG. 9 are acquired.

Figure 10:
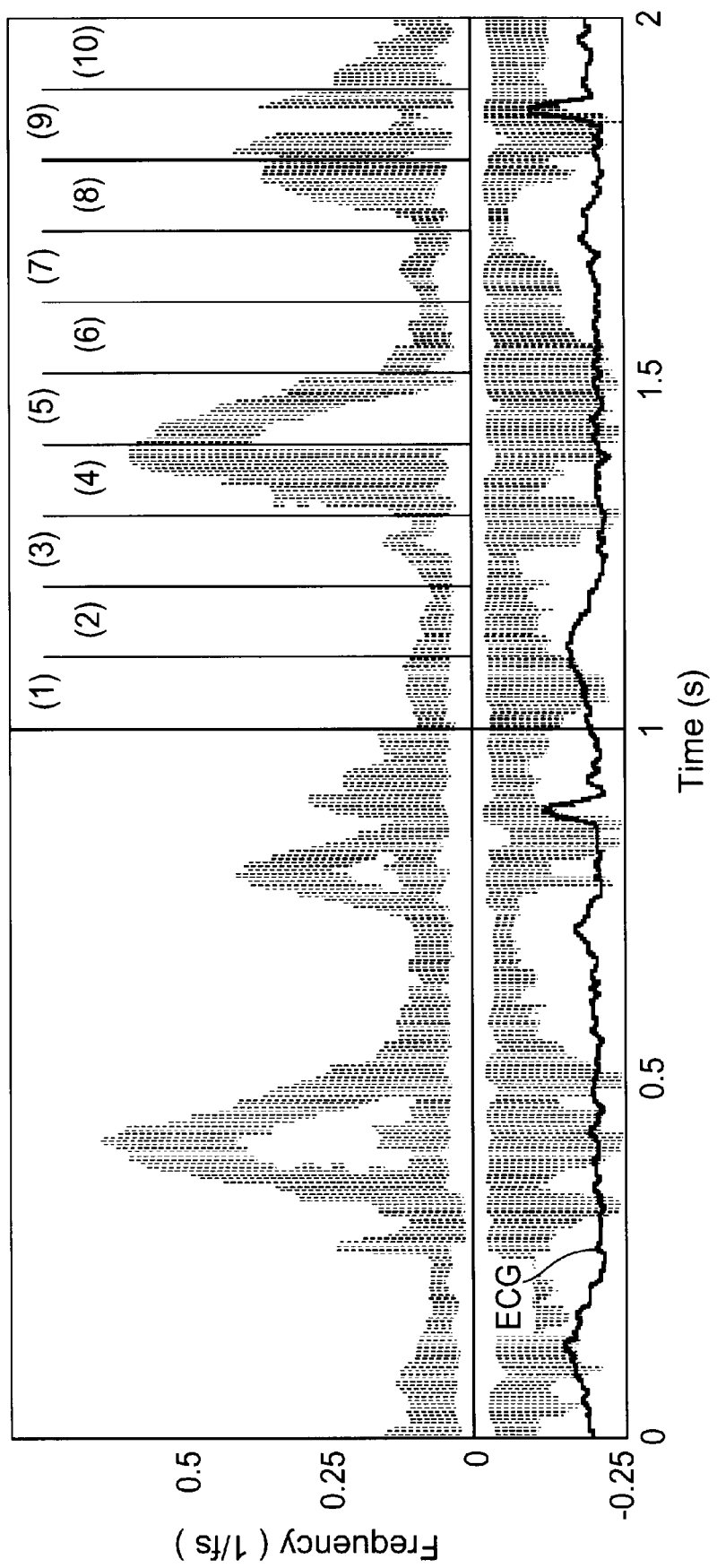
FIG. 10 is a diagram showing one example of the result of simulation.

Here, the action of the ARMAX model was simulated. This simulated result is described with reference to FIG. 10. FIG. 10 is a diagram showing one example of the simulated result. In FIG. 10, the vertical axis represents a frequency normalized with fs, and the horizontal axis represents time. For simulation, Doppler spectrum image data representing the left ventricular inflow of the heart with drastic flow rate changes was used. The interval of the segment scan was 100 ms. Between 0 second of time and 1 second of time, no segment scanning was performed, which constitutes a consecutive Doppler spectrum. A Doppler spectrum image between 1 second of time and 2 seconds of time is an image when segment scanning was carried out, which constitutes an interpolated image obtained via estimation.

In FIG. 10, the spectra in regions (1), (3), (5), (7), and (9) are estimated spectra by the ARMAX model. On the other hand, the spectra in regions (2), (4), (6 ), (8) and (10) are actual spectra that have actually been acquired by Doppler scanning. From this simulated result, it is found that in the blood flow image within the heart with drastic velocity changes, a stable Doppler spectrum image can be obtained even if the interval of segment scanning is large.

In addition, the controller 13 outputs ECG signals received from the electrocardiograph to the display controller 9, and the display controller 9 may cause these ECG signals to be displayed on the display 11 together with the Doppler spectrum images 310, 320. The display controller 9 matches the scale of the time axis in order to cause the ECG signals and Doppler spectrum images 310, 320 to be displayed side by side on the display 11.

In addition, the display processor 7 receives the Doppler spectrum image data after interpolation from the interpolator 6 in order to trace the margins of the Doppler spectrum image, generating a trace waveform. Specifically, the display processor 7 generates the trace waveform of Vp by tracing, in the time direction, the maximum velocity Vp of the waveform represented in the Doppler spectrum image that has been output by the interpolator 6. This causes the trace waveform of the maximum velocity Vp equal to waveform with the margins of the Doppler spectrum image being traced. For example, the display processor 7 generates the trace waveform representing the velocity of the left ventricular outflow by tracing the margins of the waveform represented in the Doppler spectrum image 310. In addition, the display processor 7 generates the trace waveform representing the velocity of the left ventricular inflow by tracing the margins of the waveform represented in the Doppler spectrum image 320. Then, the display controller 9 causes the trace waveform of the left ventricular blood outflow and the trace waveform of the left ventricular blood inflow to be displayed on the display 11. For example, the display controller 9 causes the Doppler spectrum image and the trace waveform to overlap and be displayed on the display 11. In addition, the display processor 7 outputs the trace waveform of the Doppler spectrum image 310 and the trace waveform of the Doppler spectrum image 320 to the computing part 8.

Combining Process

Figure 11:
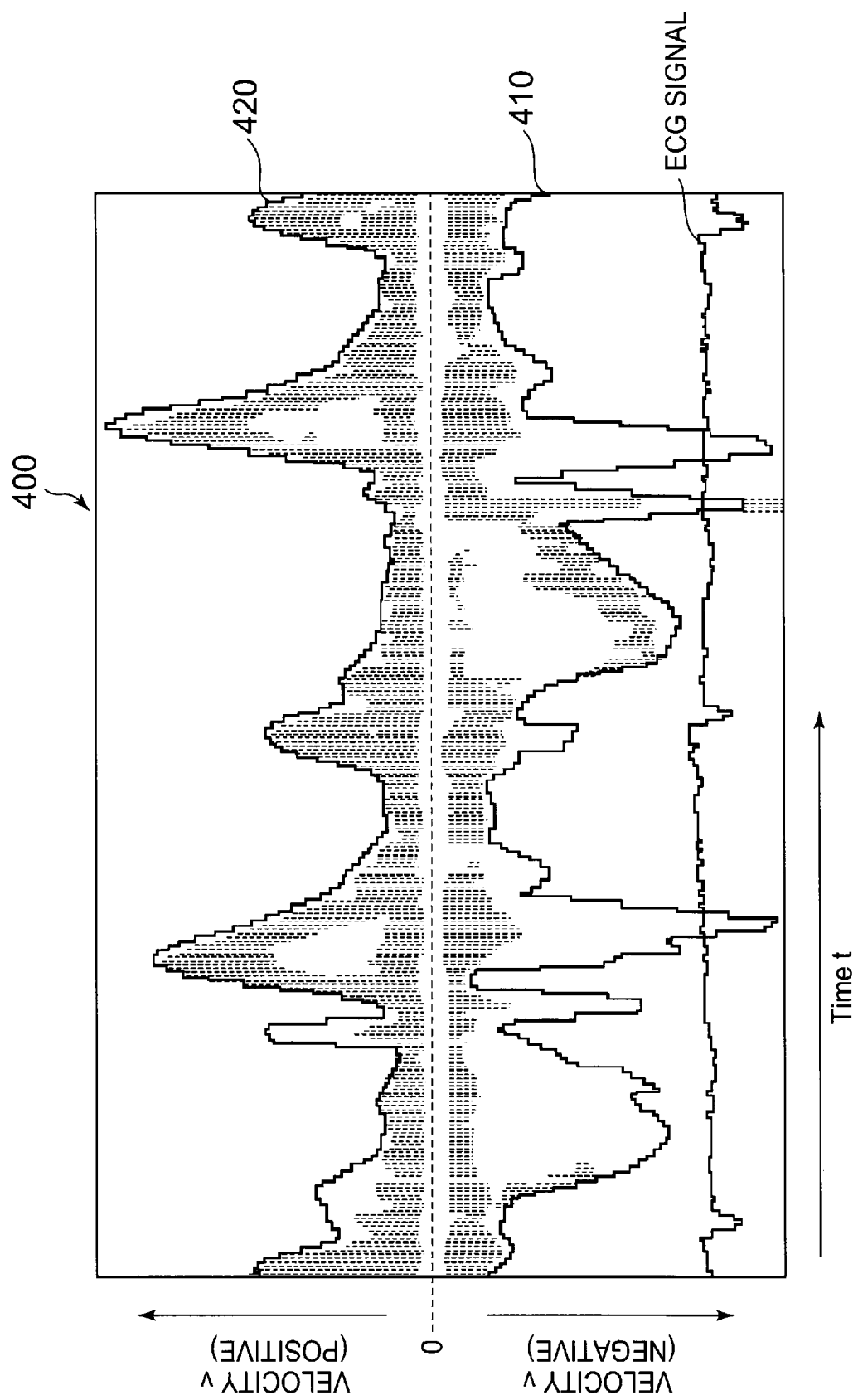
FIG. 11 is a diagram showing one example of a Doppler spectrum image acquired by the ultrasonic imaging apparatus according to an embodiment of the present invention.

In the present embodiment, two Doppler spectrum images may be combined so as to generate one Doppler spectrum image and cause the Doppler spectrum image to be displayed on the display 11. This combining process is described with reference to FIG. 11. FIG. 11 is a diagram showing one example of a Doppler spectrum image acquired by the ultrasonic imaging apparatus out according to an embodiment of the present invention.

The display processor 7 receives two Doppler spectrum image data that have undergone interpolation from the interpolator 6 and synthesizes the two sets of Doppler spectrum image data, generating one Doppler spectrum image data. In the present embodiment, observation point 102 has been set at the mitral valve tip, and the Doppler spectrum image 320 at observation point 102 represents the velocity of the left ventricular inflow. Therefore, the velocity component represented in the Doppler spectrum image 320 is biased toward the positive side. On the other hand, observation point 104 has been set at the aortic valve tip, and the Doppler spectrum image 310 at observation point 104 represents the velocity of the left ventricular outflow. Therefore, the velocity component represented in the Doppler spectrum image 310 is biased toward the negative side.

Thus, in the present embodiment, one Doppler spectrum image is generated using the positive velocity component for the Doppler spectrum image 320 at observation point 102, and using the negative velocity component for the Doppler spectrum image 310 at observation point 104.

The display processor 7 extracts an image representing the positive side of the velocity components from the Doppler spectrum image 320 at observation point 102, and extracts an image representing the negative side of the velocity components from the Doppler spectrum image 310 at observation point 104. Then, the display processor 7 generates one Doppler spectrum image data by combining the Doppler spectrum image data representing the positive side of the velocity components and the Doppler spectrum image data representing the negative side of the velocity components. The display processor 7 outputs the combined Doppler spectrum image data to the display controller 9. The display controller 9 causes the combined Doppler spectrum image to be displayed on the display 11. In addition, the display processor 7 corresponds to one example of the "combining part" according to the present invention.

One example of the combined Doppler spectrum images is shown in FIG. 11. In FIG. 11, the horizontal axis represents time (t) and the vertical axis represents blood flow velocity (v). A Doppler spectrum image 410 is an image representing the negative side of velocity components extracted from the Doppler spectrum image 310 at observation point 104. On the other hand, a Doppler spectrum image 420 is an image representing the positive side of velocity components extracted from the Doppler spectrum image 320 at observation point 102. The display processor 7 generates one Doppler spectrum image 400 by combining the Doppler spectrum image 420 representing the positive side of the velocity components and the Doppler spectrum image 410 representing the negative side of the velocity components.

The display controller 9 causes the Doppler spectrum image 400 to be displayed on the display 11. In addition, the display controller 9 may receive ECG signals output from the controller 13 and cause the Doppler spectrum image 400 and the ECG signals to be displayed on the display 11 simultaneously. The display controller 9 matches the scale of the time axis and causes the ECG signals and the Doppler spectrum image 400 to be displayed side by side on the display 11.

As described above, by combining the Doppler spectrum image 410 representing the velocity of the left ventricular outflow and the Doppler spectrum image 420 representing the velocity of the left ventricular inflow into one Doppler spectrum image to be displayed, the operator can easily ascertain the velocity of the left ventricular outflow and the velocity of the left ventricular inflow in the same time phase. That is, without observing separate Doppler spectrum images, the velocity of the left ventricular outflow and the velocity of the left ventricular inflow can be comprehended by observing only one Doppler spectrum image. In addition, there is an effect in which the calculation of indices such as the left ventricular ejection fraction (E/F) used for the evaluation of the cardiac function will become easier.

In addition, the display processor 7 may cause the trace waveform representing margins of the Doppler spectrum image 310 to overlap the Doppler spectrum image 410 and cause the trace waveform representing margins of the Doppler spectrum image 320 to overlap the Doppler spectrum image 420 and be displayed on the display 11.

Moreover, the display processor 7 outputs, to the computing part 8, the trace waveform in which the trace waveform of the Doppler spectrum image 310 and the trace waveform of the Doppler spectrum image 320 are combined.

In addition, the display processor 7 may variously assign different colors to two Doppler spectrum images. For example, colors assigned depending on the symbols of the velocity components are pre-set in the display processor 7. The display processor 7 then assigns colors to two Doppler spectrum images based on that setting.

By way of example, the display processor 7 assigns blue to a Doppler spectrum image with a velocity component becoming minus, and assigns red to a Doppler spectrum image with a velocity component becoming plus. Because the Doppler spectrum image 410 representing the velocity of the left ventricular outflow has a velocity component becoming minus, the display processor 7 assigns blue to the Doppler spectrum image 410. On the other hand, because the Doppler spectrum image 420 representing the velocity of the left ventricular inflow has a velocity component becoming plus, the display processor 7 assigns red to the Doppler spectrum image 420. This causes the Doppler spectrum image 410 to be displayed in blue and the Doppler spectrum image 420 to be displayed in red. This enables the operator to clearly distinguish and recognize the Doppler spectrum image 410 representing the velocity of the left ventricular outflow and the Doppler spectrum image 420 representing the velocity of the left ventricular inflow. In addition, the display processor 7 corresponds to one example of the "color-assigning part" according to the present invention.

Calculating the Indices

The computing part 8 receives the trace waveform of a Doppler spectrum image from the display processor 7 to obtain indices used for the evaluation of the cardiac function based on that trace waveform.

Figure 12:
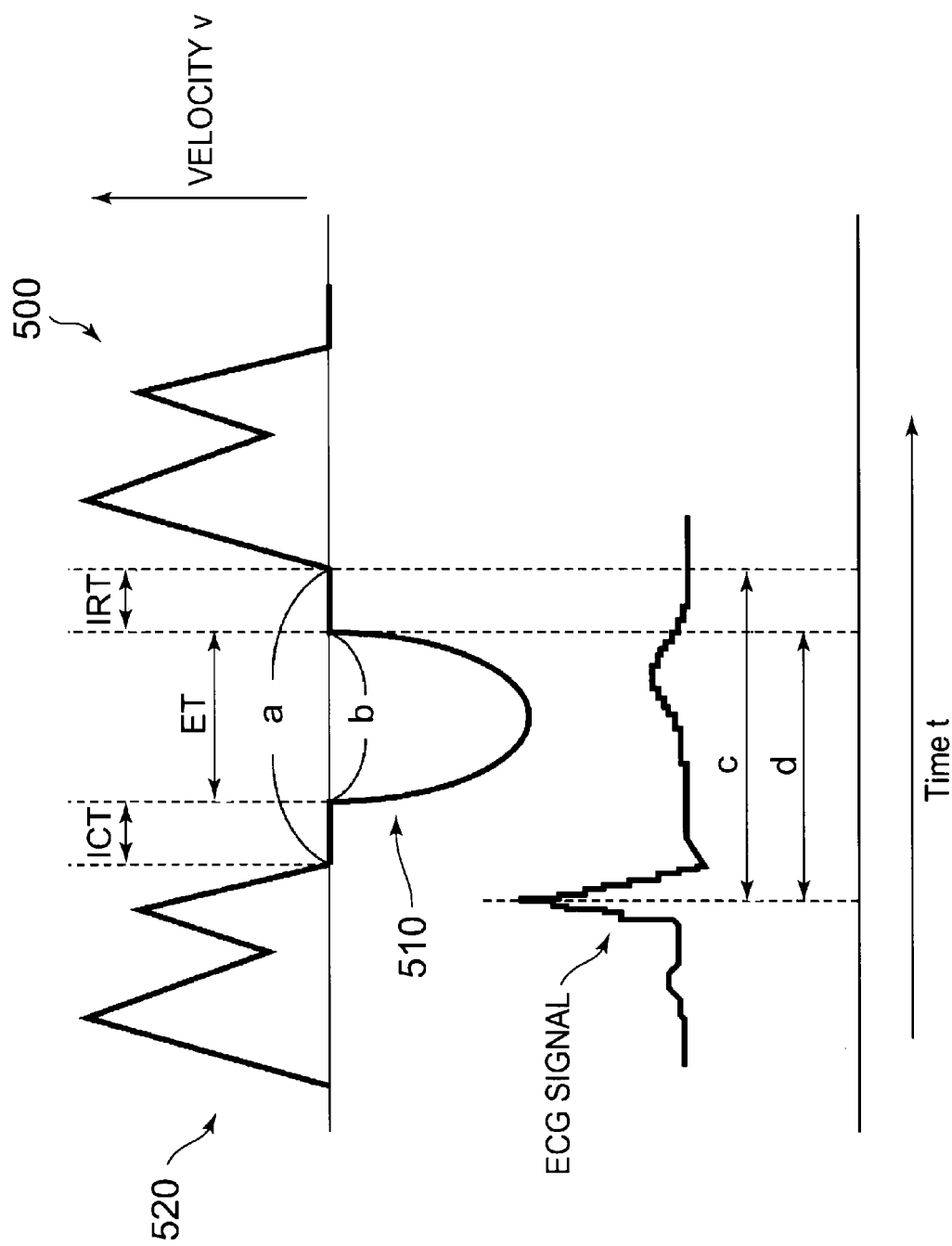
FIG. 12 is a diagram illustratively showing the trace waveform of the Doppler spectrum image.

For example, the computing part 8 receives the trace waveform representing margins of the Doppler spectrum image 310 representing the left ventricular outflow, and the trace waveform representing margins of the Doppler spectrum image 320 representing the left ventricular inflow to obtain indices. Specifically, the computing part 8 obtains indices such as the left ventricular ejection fraction (E/F) and the Tei-Index. Now, one example of the indices will be described with reference to FIG. 12. FIG. 12 is a diagram illustratively showing the trace waveform of a Doppler spectrum image.

For example as shown in FIG. 12, the display processor 7 outputs, to the computing part 8, a trace waveform 500 in which the trace waveform 510 of the Doppler spectrum image 310 and the trace waveform 520 of the Doppler spectrum image 320 are combined. The computing part 8 obtains indices based on trace waveform 500. In addition, in FIG. 12, the horizontal axis represents time (t) and the vertical axis of trace waveform 500 represents the blood flow velocity (v).

The controller 13 outputs ECG signals received from the electrocardiograph to the computing part 8, and the computing part 8 specifies a time phase of E-wave, a time phase of A-wave, and a time phase of the S-wave based on these ECG signals. Then, the computing part 8 obtains the velocity in a time phase when the E-wave is detected (E wave peak value) based on trace waveform 520 of the Doppler spectrum image 420 representing the positive side of the velocity components of the blood flow. Moreover, the computing part 8 obtains the velocity in a time phase when the A-wave is detected (A-wave peak value) based on trace waveform 520. Then, the computing part 8 obtains a value in which the E-wave peak value is divided by the A-wave peak value (E/A). Furthermore, the computing part 8 may obtain the decay time of the E-wave (DcT).

Moreover, the computing part 8 may obtain the velocity in a time phase when the S-wave is detected (S-wave peak value) based on trace waveform 510 of the Doppler spectrum image 410 representing the negative side of the velocity components of the blood flow.

Moreover, the computing part 8 may obtain the area of the aortic ejection blood flow velocity (VTI value).

Furthermore, the computing part 8 may obtain the time "a" from the ending point to the restarting point of the left ventricular inflow, the duration "b" of the left ventricular ejection blood flow=ET, the isovolumic contraction time (ICT), and the isovolumic relaxation time (IRT) based on trace waveform 500.

The computing part 8 outputs the indices to the display controller 9. The display controller 9 causes the indices obtained by the computing part 8 to be displayed on the display 11. For example, the display controller 9 causes the indices to be displayed on the display 11 together with the Doppler spectrum image.

In addition, the abovementioned indices are used as examples, and the computing part 8 may obtain other indices. Moreover, the computing part 8 may obtain all of the abovementioned indices, and may obtain indices designated by the operator. The operator designates desired indices by means of the operating part 12, and the computing part 8 obtains the designated indices.

According to the ultrasonic imaging apparatus 1 of the present embodiment, because the velocity of the left ventricular inflow and the velocity of the left ventricular outflow are each obtained from the same heartbeat, the abovementioned indices may be stably obtained even when the heart rate varies. Moreover, it is possible to attempt to improve reproducibility of the indices.

The user interface (UI) comprises the display 11 and the operating part 12. The display 11 comprises a monitor such as CRT and a liquid crystal display, with cross-sectional images, three-dimensional images, Doppler spectrum images, and the like displayed on the screen.

This operating part 12 comprises a keyboard, a mouse, a trackball, a TCS (Touch Command Screen), etc. The operator may set an observation point (range gate) by means of the operating part 12.

Moreover, the controller 13 is connected to each part of the ultrasonic imaging apparatus 1 to control movement of each part. For example, the controller 13 controls ultrasound transmitted and received by the transmitting/receiving part 3, thereby causing the ultrasound to be variously transmitted toward and received from a plurality of observation points at a plurality of times.

Second Example of Setting

Figure 13:
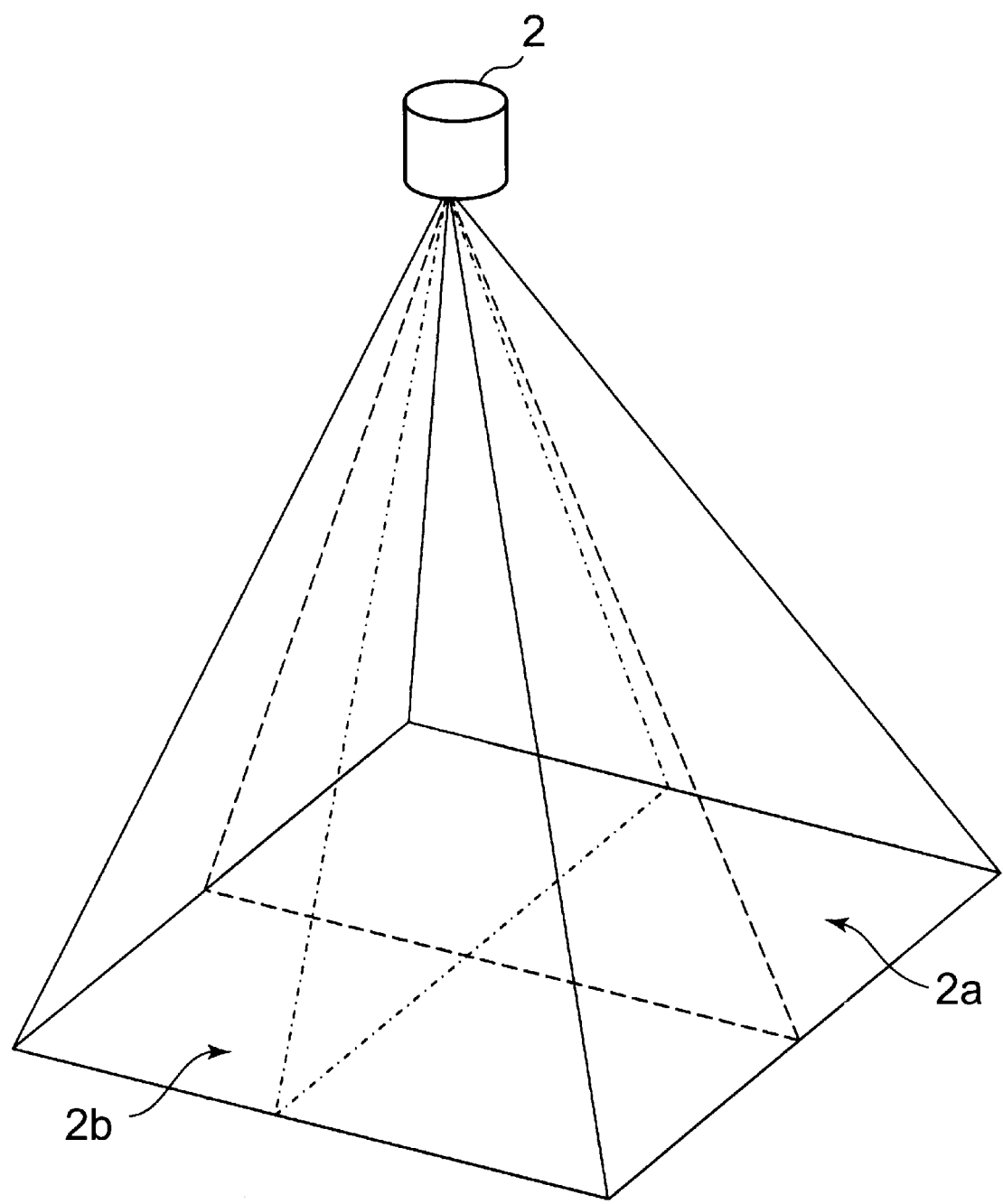
FIG. 13 is a diagram illustratively showing a cross-section scanned via the ultrasound.

Next, the second example of setting is described with reference to FIG. 13 and FIG. 14. FIG. 13 is a diagram illustratively showing a cross-section scanned via ultrasound. FIG. 14 is a diagram for describing the second example of setting an observation point, the diagram illustratively showing a cross-sectional image. In the second example setting, two cross-sectional images in cross-sections that are different from each other are acquired and displayed on the display 11.

Then, a plurality of observation points is set by setting an observation point (range gate) on each cross-sectional image.

In the abovementioned first example of setting, a plurality of observation points (range gates) are set on one cross-sectional image.

For example, one cross-sectional image in which the mitral valve tip and the aortic valve tip are represented is acquired and displayed on the display 11, and the mitral valve tip and the aortic valve tip are designated on that cross-sectional image. Thus, when a plurality of sites from which one would like to measure the blood flow are represented in one cross-sectional image, a plurality of observation points (range gates) may be set on that one cross-sectional image.

On the other hand, when a plurality of sites from which one would like to measure the blood flow is not represented in one cross-sectional image and it is difficult to set a plurality of observation points (range gates) on one cross-sectional image, a plurality of observation points (range gates) may be set as in this second example of setting. That is, two cross-sectional images in cross-sections that are different from each other are acquired and displayed on the display 11, and a plurality of observation points (range gates) are set by setting an observation point (range gate) on each cross-sectional image.

By using a 2D array probe for the ultrasonic probe 2, a plurality of cross-sections may be scanned using ultrasound. For example as shown in FIG. 13, by scanning cross-section 2a and cross-section 2b transecting each other using ultrasound, a set of cross-sectional image data in cross-section 2a and that in cross-section 2b may be acquired (multi plane scan).

For example, coordinate information of a cross-section to be scanned using ultrasound is pre-stored in the memory device of the controller 13 as a scanning condition. The operator may arbitrarily select a cross-section to be scanned using ultrasound by means of the operating part 12. Then, the controller 13 causes each cross-section to be alternately scanned by the transmitting/receiving part 3. The transmitting/receiving part 3 scans cross-section 2a and cross-section 2b alternately using ultrasound under the control of the controller 13, thereby obtaining signals received from cross-section 2a and signals received from cross-section 2b,. The received signals in each cross-section are treated via a predetermined process performed by the B-mode processor 41 and are output to the image generator 5. The image generator 5 generates cross-sectional image data for cross-section 2a and cross-sectional image data for cross-section 2b.

The display controller 9 causes a cross-sectional image of each cross-section to be displayed on the display 11.

For example as shown in FIG. 14, the display controller 9 causes cross-sectional image 110 based on the cross-sectional image data in cross-section 2a and cross-sectional image 120 based on the cross-sectional image data in cross-section 2b to simultaneously be displayed side by side on the display 11. In this second example of setting, it may be preferable for the mitral valve tip to be represented in one of the two cross-sectional images 110, 120 and the aortic valve tip to be represented in the other cross-sectional image. In other words, when it is difficult to represent the mitral valve tip and the aortic valve tip in one cross-sectional image, the mitral valve tip and the aortic valve tip are displayed using two cross-sectional images, with an observation point (range gate) set on each cross-sectional image.

Therefore, the position and angle of the ultrasonic probe 2 on the subject are changed, and the position of the cross-section to be scanned is changed so that the mitral valve tip is represented in one of the two cross-sectional images 110, 120 and the aortic valve tip is represented in the other cross-sectional image.

The operator designates the position of the mitral valve tip and the position of the aortic valve tip by means of the operating part 12 while observing cross-sectional image 110 and cross-sectional image 120 displayed on the display 11. For example, the display controller 9 causes an observation point 112 movable on cross-sectional image 110 to be displayed on the display 11 and causes an observation point 122 movable on cross-sectional image 120 to be displayed on the display 11.

Observation point 112 and observation point 122 each have predetermined sizes. The range of each predetermined size may be designated using observation point 112 and observation point 122. The operator designates the position of the mitral valve tip and the position of the aortic valve tip with observation point 112 and observation point 122. The display controller 9 causes a linear sample line 111 showing the direction of the transmission and reception of ultrasound to overlap cross-sectional image 110, and causes sample line 121 to overlap cross-sectional image 120 and be displayed on the display 11. The operator may move sample line 111 and sample line 121 in the scanning direction (direction of arrow A) by means of the operating part 12. Moreover, the operator may move observation point 112 on sample line 111 in the direction of the transmission and reception of ultrasound (direction of arrow B) by means of the operating part 12.

Similarly, the operator may move observation point 122 on sample line 121 in the direction of transmission and reception by means of the operating part 12.

For example, the position and angle of the ultrasonic probe 2 on the subject are changed and the position of the cross-section to be scanned is changed so that the mitral valve tip is represented in cross-sectional image 110 and the aortic valve tip is represented in cross-sectional image 120. Then, the operator moves sample line 111 to the position of the mitral valve tip by means of the operating part 12 while observing cross-sectional image 110, and designates the position of the mitral valve tip by means of observation point 112 by moving observation point 112 in the direction of transmission and reception (direction of arrow B). Similarly, the operator moves sample line 121 to the position of the aortic valve tip by means of the operating part 12 while observing cross-sectional image 120, and moreover designates the position of the aortic valve tip by means of observation point 122 by moving observation point 122 in the direction of transmission and reception (direction of arrow B). Thus, when sites from which one would like to observe the blood flow are designated by the observation points 112, 122, coordinate information showing the position of observation point 112 on cross-sectional image 110, and coordinate information showing the position of observation point 122 on cross-sectional image 120 are output via the user interface (UI) 10 to the controller 13.

Moreover, as with the first example of setting, angle markers are caused to overlap cross-sectional image 110 and cross-sectional image 120 and be displayed. By designating the orientation of the blood flow using the angle mark, the angle formed by the blood flow at the site where observation point 112 has been set and the direction of the transmission and reception of ultrasonic beam are obtained on cross-sectional image 110. Moreover, the angle formed by the blood flow at the site where observation point 122 has been set and the direction of the transmission and reception of ultrasonic beam are obtained on cross-sectional image 120. The Doppler processor 42 variously obtains the blood flow velocity at observation point 112 and observation point 122 using the angles.

Cross-sectional image 110 is an image acquired by scanning cross-section 2a, and cross-sectional image 120 is an image acquired by scanning cross-section 2b. Coordinate information in the three-dimensional space of cross-section 2a has been specified in the controller 13. The controller 13 specifies a coordinate of observation point 112 in three-dimensional space based on the coordinate information of observation point 112 on cross-sectional image 110 (cross-section 2a). Similarly, the coordinate information in the three-dimensional space of cross-section 2b has been specified in the controller 13. The controller 13 specifies a coordinate of observation point 122 in three-dimensional space based on the coordinate information of observation point 122 on cross-sectional image 120 (cross-section 2b). Next, the controller 13 outputs the coordinate information of observation point 112 and observation point 122 to the transmitting/receiving part 3 and the Doppler processor 42.

Then, as with the abovementioned first example of setting, the transmitting/receiving part 3 obtains Doppler information at observation point 112 and Doppler information at observation point 122. Doppler processor 42 obtains the blood flow velocity at observation point 112 and the blood flow velocity at observation point 122 based on the Doppler information obtained by the transmitting/receiving part 3. Furthermore, in the second example of setting, as with the abovementioned first example of setting, the transmitting/receiving part 3 performs a segment scan under the control of the controller 13. In other words, as shown in FIG. 5, under the control of the controller 13, the transmitting/receiving part 3 serially transmits and receives ultrasound toward and from observation point A (observation point 112) at N times, and subsequently, serially transmits and receives ultrasound toward and from observation point B (observation point 122) at N times. The transmitting/receiving part 3 continues to variously transmit and receive ultrasound alternatively toward and from observation point A (observation point 112) and observation point B (observation point 122) at N times. Then, under the control of the controller 13, the Doppler processor 42 consecutively generates a Doppler spectrum image at observation point 112 (observation point A) and a Doppler spectrum image at observation point 122 (observation point B).

As described above, by representing the mitral valve tip and the aortic valve tip using two cross-sectional images when it is difficult to represent the mitral valve tip and the aortic valve tip in one cross-sectional image, observation points can be set for each. Thus, if it is difficult to represent a plurality of sites from which one would like to measure the blood flow velocity in one cross-sectional image, each site may be represented with two cross-sectional images, with an observation point set for each cross-sectional image. Furthermore, in the second example of setting, by transmitting and receiving ultrasound alternatively toward and from each observation point at a plurality of times (N times) respectively as with the abovementioned first example of setting, a Doppler spectrum image at each observation point can be acquired without reducing the Doppler velocity range.

Then, as with the abovementioned first example of setting, a data-missing part in the Doppler spectrum image data is interpolated by the interpolator 6. The display controller 9 causes a Doppler spectrum image that has undergone interpolation to be displayed on the display 11. In the second example of setting, a Doppler spectrum image from observation point 112 and a Doppler spectrum image from observation point 122 are generated and displayed on the display 11. Moreover, the display processor 7 generates the trace waveform of Doppler spectrum image data at each observation point that has undergone interpolation.

The computing part 8 obtains the indices used for the evaluation of the cardiac function based on the trace waveform at each observation point. In addition, the display processor 7 may generate one set of Doppler spectrum image data by combining Doppler spectrum image data at each observation point that has undergone interpolation.

Moreover, volume data may be obtained by performing a volume scan with the ultrasonic probe 2 and the transmitting/receiving part 3.

Then, the image generator 5 may subject the volume data to MPR processing to generate MPR image data in which the mitral valve tip is represented and MPR image data in which the aortic valve tip is represented.

For example, the image generator 5 generates three-dimensional image data sterically representing the heart of the subject by subjecting the volume data to volume rendering. The display controller 9 causes a three-dimensional image based on that three-dimensional data to be displayed on the display 11. The operator designates an arbitrary cross-section by means of the operating part 12 while observing the three-dimensional image displayed on the display 11. In the second example of setting, the operator designates the positions of two cross-sections by means of the operating part 12 so that the mitral valve tip is included in one cross-section and the aortic valve tip is included in the other cross-section. Then, the image generator 5 receives coordinate information of the two cross-sections from the user interface (UI) 10 and subjects the volume data to MPR processing, thereby generating cross-sectional image data (MPR image data) for each cross-section. The display controller 9 causes a cross-sectional image of each cross-section to be displayed on the display 11. The operator observes two cross-sectional images in order to adjust the positions of the two cross-sections so that the mitral valve tip is included in one cross-sectional image and the aortic valve tip is included in the other cross-sectional image.

Then, as shown in FIG. 14, the display controller 9 causes cross-sectional image 110 (MPR image) in which the mitral valve tip is represented and cross-sectional image 120 (MPR image) in which the aortic valve tip is represented to be displayed on the display 11. The operator designates the position of the mitral valve tip and the position of the aortic valve tip via observation point 112 and observation point 122 by means of the operating part 12.

Moreover, the image generator 5 may generate three-dimensional image data sterically representing the heart of the subject by subjecting the volume data to volume rendering. The display controller 9 causes two observation points (range gates) to overlap a three-dimensional image based on that three-dimensional image data and be displayed on the display 11. The operator may designate the position of the mitral valve tip and the position of the aortic valve tip via the two observation points by means of the operating part 12 while observing the three-dimensional image of the heart displayed on the display 11.

Third Example of Setting

In the abovementioned first and second examples of setting, a case in which two sites are designated using two observation points (range gates) has been described. In the third example of setting, a plurality of sites is designated using three or more observation points.

Figure 15:
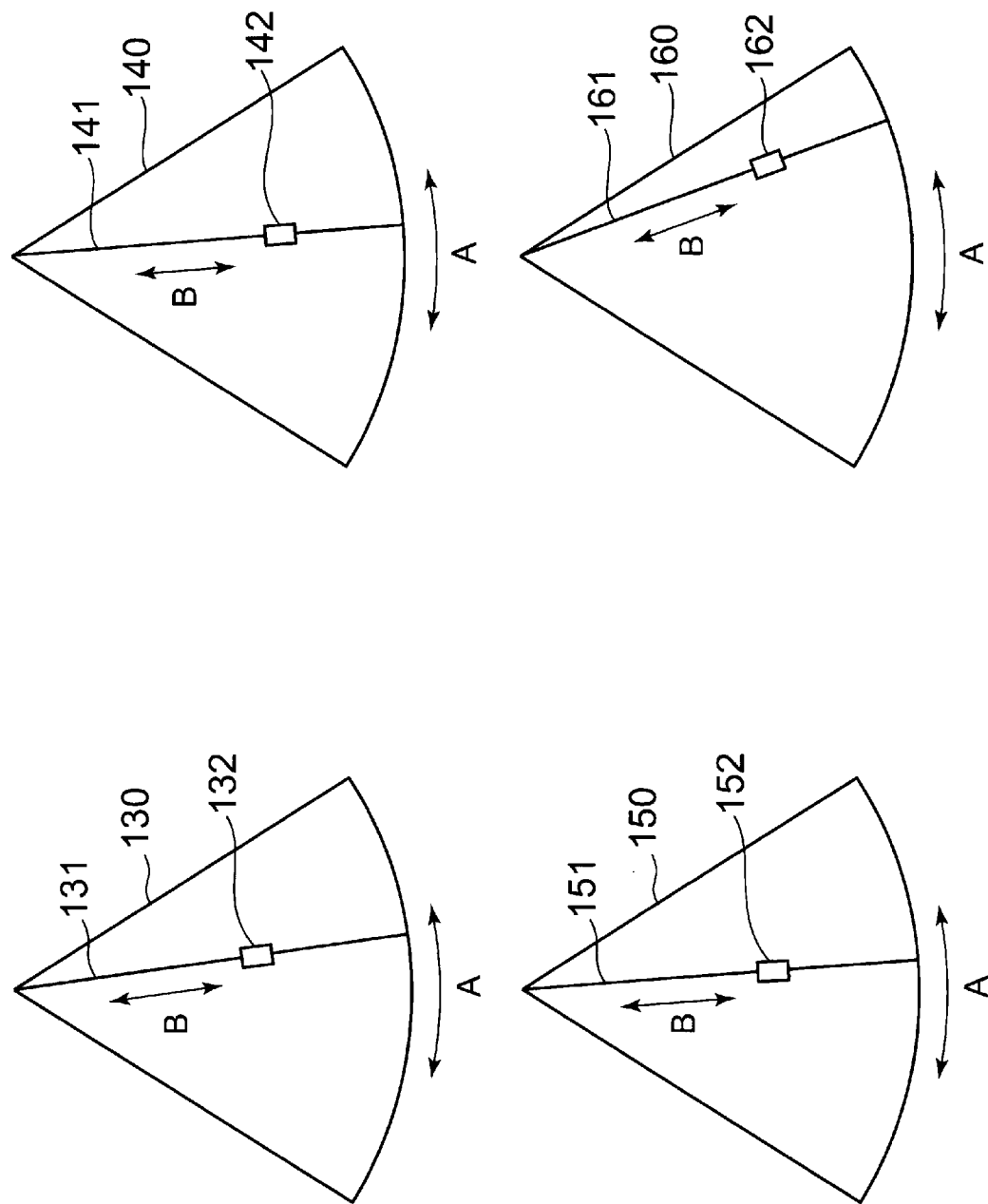
FIG. 15 is a diagram for describing the third example of setting an observation point, the diagram illustratively showing a cross-sectional image.

The third example of setting is described with reference to FIG. 15. FIG. 15 is a diagram for describing the third example of setting an observation point, the diagram illustratively showing an cross-sectional image. By way of example, a case in which four sites are designated with four observation points will be described. For example, four cross-sectional images in cross-sections that are different from each other are acquired and displayed on the display 11, and observation points are set on each cross-sectional image, thereby setting a plurality of observation points.

In addition to measuring the left ventricular inflow and the left ventricular outflow, measuring the pulmonary vein blood flow and the pulmonary artery blood flow is also suitable for evaluating the cardiac function. Then, in order to measure the pulmonary venous blood flow and the pulmonary arterial blood flow in addition to the left ventricular inflow and the left ventricular outflow, it is necessary to set observation points at a total of four sites. It may be difficult to set a plurality of observation points (range gates) in one cross-sectional image, as those four sites are not represented in one cross-sectional image. In that case, as in this third example of setting, four cross-sectional images of cross-sections that are different from each other are acquired and displayed on the display 11, and observation points are set on respective cross-sectional images, thereby setting four observation points.

Volume data is acquired by performing volume scanning with the ultrasonic probe 2 and the transmitting/receiving part 3. The image generator 5 generates cross-sectional image data (MPR image data) in cross-sections that are different from each other by subjecting the volume data to MPR processing. In the third example of setting, the image generator 5, by way of example, generates MPR image data in four cross-sections transecting each other. For example, the image generator 5 generates MPR image data in which the mitral valve tip is represented, MPR image data in which the aortic valve tip is represented, MPR image data in which the pulmonary venous blood flow is represented, and MPR image data in which the pulmonary arterial blood flow is represented.

For example, the image generator 5 generates three-dimensional image data sterically representing the heart of the subject by subjecting the volume data to volume rendering. The display controller 9 causes a three-dimensional image based on that three-dimensional image data to be displayed on the display 11. The operator designates four cross-sections by means of the operating part 12 while observing the three-dimensional image displayed on the display 11. In the third example of setting, the operator designates the positions of the four cross-sections by means of the operating part 12 so that, among the four cross-sections, the mitral valve tip is included in the first cross-section, the aortic valve tip is included in the second cross-section, the pulmonary vein blood flow is included in the third cross-section, and the pulmonary artery blood flow is included in the fourth cross-section. Then, the image generator 5 receives coordinate information of the four cross-sections from the user interface (UI) 10 and subjects the volume data to MPR processing, thereby generating cross-sectional image data (MPR image data) for each cross-section.

The display controller 9 causes a cross-sectional image of each cross-section to be displayed on the display 11. The operator observes four cross-sectional images in order to adjust the positions of the four cross-sections so that the mitral valve tip is included in the first cross-sectional image, the aortic valve tip is included in the second cross-sectional image, the pulmonary venous blood flow is included in the third cross-sectional image, and the pulmonary arterial blood flow is included in the fourth cross-sectional image.

Then, as shown in FIG. 15, the display controller 9 causes cross-sectional image 130 in the first cross-section, cross-sectional image 140 of the second cross-section, cross-sectional image 150 of the third cross-section, and cross-sectional image 160 of the fourth cross-section to be displayed on the display 11. In this third example of setting, the operator adjusts the positions of the four cross-section so that any one of the mitral valve tip, the aortic valve tip, the pulmonary venous blood flow, and the pulmonary arterial blood flow would be included in each of the four cross-sectional images 130, 140, 150, 160. For example, the operator adjusts the positions of the four cross-section so that the mitral valve tip is represented in cross-sectional image 130, the aortic valve tip is represented in cross-sectional image 140, the pulmonary venous blood flow is represented in cross-sectional image 150, and the pulmonary arterial blood flow is represented in cross-sectional image 160. Then, an observation point (range gate) is set in each cross-sectional image.

That is, using four cross-sectional images, the mitral valve tip, the aortic valve tip, the pulmonary venous blood flow, and the pulmonary arterial blood flow are displayed, with an observation point set for each.

The operator designates the position of the mitral valve tip, the position of the aortic valve tip, the position of the pulmonary venous blood flow, and the position of the pulmonary arterial blood flow by means of the operating part 12 while observing the cross-sectional images 130, 140, 150, 160 displayed on the display 11. For example, the display controller 9 causes sample line 131 and observation point 132 to overlap cross-sectional image 130 and be displayed on the display 11. The operator designates the position of the mitral valve tip with observation point 132. Similarly, the display controller 9 causes sample line 141 and observation point 142 to overlap cross-sectional image 140 and be displayed on the display 11. Moreover, the display controller 9 causes sample line 151 and observation point 152 to overlap cross-sectional image 150 and be displayed on the display 11.

Furthermore, the display controller 9 causes sample line 161 and observation point 162 to overlap cross-sectional image 160 and be displayed on the display 11. The operator, by means of operating part 12, moves each sample line in the scanning direction (direction of arrow A), and further moves each observation point in the direction of the transmission and reception of ultrasound (direction of arrow B), thereby designating the position of the mitral valve tip, the position of the aortic valve tip, the position of the pulmonary venous blood flow, and the position of the pulmonary arterial blood flow with an observation point on each cross-sectional image.

In addition, as with the first example of setting, an angle marker is caused to overlap each of the cross-sectional images 130, 140, 150, 160 and be displayed. By designating the orientation of the blood flow with each angle mark, the angle formed by the blood flow at a site where each observation point has been set and the direction of the transmission and reception of an ultrasonic beam is obtained for each cross-sectional image. The Doppler processor 42 variously obtains the blood flow velocity at the observation points 132, 142, 152, 162 using each angles.

Thus, when sites from which one would like to observe the blood flow are designated using the observation points 132, 142, 152, 162, coordinate information showing the position of the observation point on each cross-sectional image is output from the user interface (UI) 10 to the controller 13. The controller 13 outputs coordinate information of the four observation points to the transmitting/receiving part 3 and the Doppler processor 42.

Then, as with the abovementioned first example of setting, the transmitting/receiving part 3 acquires Doppler information at the observation points 132, 142, 152, 162. The Doppler processor 42 obtains the blood flow velocity at the observation points 132, 142, 152, 162 based on the Doppler information acquired by the transmitting/receiving part 3. Further-more, in the third example of setting, as with the abovementioned first example of setting, the transmitting/receiving part 3 performs segment scanning under the control of the controller 13. For example, under the control of the controller 13, the transmitting/receiving part 3 serially transmits and receives ultrasound toward and from observation point 132 at N times.

Subsequently, it serially transmits and receives ultrasound toward and from observation point 142 at N times. Thereafter, it serially transmits and receives ultrasound toward and from observation point 152 at N times, and finally, it serially transmits and receives ultrasound toward and from observation point 162 at N times. The transmitting/receiving part 3 continues to serially transmit and receive ultrasound toward and from the observation points 132, 142, 152, 162 at each N time. Then, under the control of the controller 13, the Doppler processor 42 generates a Doppler spectrum image at observation point 132, a Doppler spectrum image at observation point 142, a Doppler spectrum image at observation point 152, and a Doppler spectrum image at observation point 162 in series.

As described above, when it is difficult to represent the mitral valve tip, the aortic valve tip, the pulmonary venous blood flow, and the pulmonary arterial blood flow in one cross-sectional image, by representing the mitral valve tip, the aortic valve tip, the pulmonary venous blood flow, and the pulmonary arterial blood flow using four cross-sectional images, an observation point can be set for each.

Furthermore, in the third example of setting, as with the first example of setting, by serially transmitting and receiving ultrasound toward and from each observation point at a plurality of times (N times), a Doppler spectrum image at each observation point can be acquired without reducing the Doppler velocity range.

Then, as with the first example of setting, a data-missing part in Doppler spectrum image data is interpolated by the interpolator 6. The display controller 9 causes a Doppler spectrum image that has been subjected to interpolation to be displayed on the display 11. In the third example of setting, Doppler spectrum images variously of observation point 132, observation point 142, observation point 152, and observation point 162 are generated and displayed on the display 11. In other words, Doppler spectrum images at four sites are generated and displayed on the display 11. Moreover, the display processor 7 generates the trace waveform of a Doppler spectrum image at each observation point that has been subjected to interpolation. The computing part 8 obtains indices used for evaluating cardiac function based on the trace waveform at each observation point.

In addition, the abovementioned signal processor 4, image generator 5, interpolator 6, display processor 7, computing part 8, display controller 9, and controller 13 each incorporate an CPU (Central Processing Unit) and memory devices such as ROM (Read Only Memory) and RAM (Random Access Memory). In the memory device, a signal-processing program for executing the function of the signal processor 4, an image-generating program for executing the function of the image generator 5, an interpolating program for executing the function of the interpolator 6, a display-composing program for executing the function of the display processor 7, a computing program for executing the function of the computing part 8, a display-controlling program for executing the function of the display controller 9, and a controlling program for executing the function of the controller 13 have been stored.

The CPU executes the signal-processing program stored in the memory device, thereby generating B-mode ultrasonic raster data or Doppler spectrum images. In addition, the CPU executes the image-generating program stored in the memory device, thereby generating ultrasonic image data such as cross-sectional image data, MPR image data, and three-dimensional image data. Moreover, the CPU executes the interpolating program stored in the memory device, thereby interpolating a data-missing part in a Doppler spectrum image.

Furthermore, the CPU executes the display-composing program stored in the memory device, thereby obtaining the trace waveform and combining two Doppler spectrum images. In addition, the CPU executes the computing program stored in the memory device, thereby obtaining indices used for evaluating the cardiac function. Moreover, the CPU executes the display-controlling program stored in the memory device, thereby causing cross-sectional images or Doppler spectrum images to be displayed on the display 11. Furthermore, the CPU executes the controlling program stored in the memory device, thereby controlling movement of each part of the ultrasonic imaging apparatus 1.

Fourth Example of Setting

In the fourth example of setting, observation points (range gates) are set at the mitral valve tip and the mitral annulus in order to obtain the velocity of the left ventricular inflow at the mitral valve tip and the velocity of the mitral annulus. The velocity of the mitral annulus tissue is obtained by performing tissue Doppler imaging (DTI).

In the fourth example of setting, a cross-sectional image of the subject is acquired and displayed on the display 11, and observation points (range gates) are set at the position of the mitral valve tip and the position of the mitral annulus represented in that cross-sectional image. For example, the display controller 9 causes cross-sectional image 100 to be displayed on the display 11. Scanning is performed while changing the position and angle of the ultrasonic probe 2 so that the mitral valve tip and the mitral annulus are represented in cross-sectional image 100.

The operator designates the position of the mitral valve tip and the position of the mitral annulus represented in cross-sectional image 100 by means of the operating part 12 while observing cross-sectional image 100 displayed on the display 11. For example, the display controller 9 causes observation point 102 and observation point 104 to be displayed on cross-sectional image 100, and the operator designates the position of the mitral valve tip and the position of the mitral annulus using observation point 102 and observation point 104, respectively. For example, the position of the mitral valve tip is designated as observation point 102, and the position of the mitral annulus is designated as observation point 104. Coordinate information showing the position of the observation point on cross-sectional image 100 is output from the user interface (UI) 10 to the controller 13. In addition, when the mitral valve tip and the mitral annulus are not represented in one cross-sectional image and it is difficult to set observation points (range gates) at the mitral valve tip and the mitral annulus in one cross-sectional image, a process according to the abovementioned second example of setting may be performed.

Specifically, a cross-sectional image in which the mitral valve tip is represented and a cross-sectional image in which the mitral annulus is represented are acquired and displayed on the display 11, and observation points (range gates) may be set on each cross-sectional image.

As with the abovementioned first example, the transmitting and receiving part 3 acquires Doppler information at observation point 102 (mitral valve tip) and Doppler information at observation point 104 (mitral annulus) by performing segment scanning. Normal Doppler scanning is performed for the mitral valve tip, and TDI is performed for the mitral annulus. The Doppler processor 42 serially generates a Doppler spectrum image at observation point 102 (mitral valve tip) and a Doppler spectrum image at observation point 104 (mitral annulus). Then, as with the first example of setting, a data-missing part in Doppler spectrum image data is interpolated by the interpolator 6. The display controller 9 causes a Doppler spectrum image subjected to interpolation to be displayed on the display 11. In the fourth example of setting, a Doppler spectrum image at the mitral valve tip (observation point 102) and a Doppler spectrum image at the mitral annulus (observation point 104) are generated and displayed on the display 11.

Because observation point 102 has been set for the position of the mitral valve tip, the Doppler spectrum image at observation point 102 represents the velocity of the left ventricular inflow at the mitral valve tip. On the other hand, because observation point 104 has been set for the position of the mitral annulus, the Doppler spectrum image at observation point 104 represents the velocity of the tissue of the mitral annulus.

Moreover, the display processor 7 generates the trace waveform of Doppler spectrum image data at each observation point that has been subjected to interpolation. In the fourth example of setting, the display processor 7 generates the trace waveform of the Doppler spectrum image data representing the velocity of the left ventricular inflow, and the trace waveform of the Doppler spectrum image data representing the velocity of the mitral annulus.

The computing part 8 obtains an index used for the evaluation of cardiac function based on the trace waveform at each observation position. In the fourth example of setting, the computing part 8 obtains an index based on the trace waveform representing margins of the Doppler spectrum image representing the velocity of the left ventricular inflow and the trace waveform representing margins of the Doppler spectrum image representing the velocity of the tissue of the mitral annulus.

For example, the computing part 8 obtains the velocity in a time phase when the E-wave is detected (E wave peak value) based on the trace waveform of the Doppler spectrum image representing the velocity of the left ventricular inflow. In addition, the computing part 8 obtains the peak value of the velocity of the mitral annulus based on the trace waveform of the Doppler spectrum image representing the velocity of the mitral annulus. Then, the computing part 8 obtains the value in which the E-wave peak value is divided by the peak value of the velocity of the mitral annulus (E/e'). The display controller 9 causes the index obtained by the computing part 8 (E/e') to be displayed on the display 11.

As described above, according to the ultrasonic imaging apparatus of the present embodiment, Doppler scanning for obtaining the velocity of the left ventricular inflow and TDI for obtaining the velocity of the mitral annulus can be combined. Thereby, (E/e'), which is the index of the left ventricular diastolic performance, can be obtained based on Doppler spectrum images of the same heartbeat.

Conventionally, (E/e') was obtained based on Doppler spectrum images of different heartbeats. In contrast, according to the ultrasonic imaging apparatus of the present embodiment, (E/e') can be obtained based on Doppler spectrum images of the same heartbeat, so cardiac enlargement and the like can be more accurately evaluated.

In addition, volume data may be acquired by performing volume scanning with the ultrasonic probe 2 and the transmitting/receiving part 3. Then, the image generator 5 may generate MPR image data in which the mitral valve tip is represented and MPR image data in which the mitral annulus is represented by subjecting the volume data to MPR processing. The display controller 9 causes a cross-sectional image in which the mitral valve tip is represented and a cross-sectional image in which the mitral annulus is represented to be displayed on the display 11, and the operator designates the position of the mitral valve tip and the position of the mitral annulus using observation points (range gates). In addition, the image generator 5 generates three-dimensional image data sterically representing the heart based on the volume data, and the display controller 9 may cause two observation points (range gates) to overlap the three-dimensional image and be displayed on the display 11. In this case, the operator designates the position of the mitral valve tip and the position of the mitral annulus using two observation points while observing the three-dimensional image displayed on the display 11.

What is claimed is:

1. An ultrasonic imaging apparatus comprising:
    a Doppler scanner configured to perform Doppler scanning by serially transmitting and receiving ultrasound toward and from each of a plurality of observation points in a subject at a plurality of respective times;
    a processor configured to generate a first Doppler spectrum image representing the velocity of a moving body at each observation point by analyzing the frequency of signals received at the plurality of observation points acquired via Doppler scanning;
    an interpolator configured to acquire a second Doppler spectrum image by interpolation based on the first Doppler spectrum image at each observation point generated by the processor, the second Doppler spectrum image being at each observation point when the ultrasound has not been transmitted to and received from each observation point by the Doppler scanner transmitting and receiving ultrasound toward and from the plurality of observation points at a plurality of respective times, and to combine the first Doppler spectrum at each observation point generated by the processor and the second Doppler spectrum image at each observation point via interpolation for each observation point, in order to generate a third Doppler spectrum at each observation point; and
    a display controller configured to cause the third Doppler spectrum image at each observation point combined by the interpolator to be displayed on a display, and wherein
    the interpolator is configured to obtain a quantity of characteristics on the first Doppler spectrum image at each observation point based on the first Doppler spectrum image at each observation point, to receive ECG signals of the sample in order to estimate the second Doppler spectrum image at each observation point via a regression model with a parametric model utilizing the ECG signal and the quantity of characteristics on the first Doppler spectrum image at each observation point, and to generate the third Doppler spectrum image at each observation point by combining the first Doppler spectrum image at each observation point and the estimated second Doppler spectrum image at each observation point per observation point.

2. The ultrasonic imaging apparatus according to Claim wherein the interpolator is configured to obtain the average flow rate of the moving body, spectral dispersion, and total power of the spectrum as the quantity of characteristics for the first Doppler spectrum image at each observation point based on the first Doppler spectrum image at each observation point.

3. The ultrasonic imaging apparatus according to claim 1, further comprising:
    a color-assigning part configured to assign a different color to the third Doppler spectrum image based on a velocity component of the third Doppler spectrum image, at each observation point combined by the interpolator for each observation point,
    wherein the display controller is configured to cause the third Doppler spectrum image at each observation point with a different color assigned to be displayed on the display simultaneously.

4. The ultrasonic imaging apparatus according to claim 1, further comprising:
    an image-acquiring part configured to acquire ultrasonic image data representing a tissue in the subject by scanning the subject using ultrasound,
    wherein the display controller is configured to cause markers for designating each of the plurality of observation points to overlap the ultrasonic image based on the ultrasonic image data and be displayed on the display; and
    the Doppler scanner is configured to perform Doppler scanning by receiving the positions of the plurality of observation points designated by the markers on the ultrasonic image, and by serially transmitting and receiving ultrasound toward and from each of the designated plurality of observation points at a plurality of respective times.

5. The ultrasonic imaging apparatus according to claim 1, further comprising:
    an image-acquiring part configured to scan the heart of the subject using ultrasound to acquire ultrasonic image data in which the mitral valve tip and the aortic valve tip in the heart of the subject are represented; and
    a combining part,
    wherein the display controller is configured to cause markers for designating the position of the mitral valve tip and the position of the aortic valve tip to each overlap the ultrasonic image based on the ultrasonic image data and be displayed on the display;
    the Doppler scanner is configured to receive the position of the mitral valve tip and the position of the aortic valve tip designated by the markers on the ultrasonic image in order to perform Doppler scanning by alternately transmitting and receiving ultrasound toward and from two observation points at a plurality of respective times, with the position of the mitral valve tip and the position of the aortic valve tip each as observation points;
    the processor is configured to generate the first Doppler spectrum image at the position of the mitral valve tip and the first Doppler spectrum image at the position of the aortic valve tip;
    the interpolator is configured to acquire the second Doppler spectrum image at the position of the mitral valve tip based on interpolation of the first Doppler spectrum image at the position of the mitral valve tip, to acquire the second Doppler spectrum image at the position of the aortic valve tip based on interpolation of the first Doppler spectrum image at the position of the aortic valve tip, and to generate the third Doppler spectrum image at the position of the mitral valve tip and the third Doppler spectrum image at the position of the aortic valve tip via the combination;
    the combining part is configured to generate a single Doppler spectrum image by combining a positive velocity component of the velocity represented in the third Doppler spectrum image at the position of the mitral valve tip and a negative velocity component of the velocity represented in the third Doppler spectrum image at the position of the aortic valve tip; and the display controller is configured to cause the single Doppler spectrum image generated by the combining part to be displayed on the display.

6. The ultrasonic imaging apparatus according to claim 5, further comprising:

a computing part configured to obtain an index used for the evaluation of cardiac function based on the third Doppler spectrum image at the position of the mitral valve tip and the third Doppler spectrum image at the position of the aortic valve tip.

7. The ultrasonic imaging apparatus according to claim 1, further comprising:

an image-acquiring part configured to scan the heart of the subject using ultrasound to acquire ultrasonic image data in which a mitral valve tip and an mitral annulus in the heart of the subject are represented, wherein the display controller is configured to cause markers for designating the position of the mitral valve tip and the position of the mitral annulus to each overlap the ultrasonic image based on the ultrasonic image data and be displayed on the display;

the Doppler scanner is configured to receive the position of the mitral valve tip and the position of the mitral annulus designated by the markers on the ultrasonic image to perform Doppler scanning by alternately transmitting and receiving ultrasound toward and from two observation points at a plurality of respective times, with the position of the mitral valve tip and the position of the mitral annulus each as observation points;

the processor is configured to generate the first Doppler spectrum image at the position of the mitral valve tip and the first Doppler spectrum image at the position of the mitral annulus;

the interpolator is configured to acquire the second Doppler spectrum image at the position of the mitral valve tip by interpolation based on the first Doppler spectrum image at the position of the mitral valve tip, to acquire the second Doppler spectrum image at the position of the mitral annulus by interpolation based on the first Doppler spectrum image at the position of the mitral annulus, and to generate the third Doppler spectrum image at the position of the mitral valve tip and the third Doppler spectrum image at the position of the mitral annulus via the combination; and the display controller is configured to cause the third Doppler spectrum image at the position of the mitral valve tip and the third Doppler spectrum image at the position of the mitral annulus that have been combined by the interpolator to be displayed on the display.

8. The ultrasonic imaging apparatus according to claim 7, further comprising:

a computing part is configured to obtain an index used for the evaluation of cardiac function based on the third Doppler spectrum image at the position of the mitral valve tip and the third Doppler spectrum image at the position of the mitral annulus.

9. The ultrasonic imaging apparatus according to claim 8, wherein the computing part is configured to obtain the peak value of the blood flow velocity at the position of the mitral valve tip based on the third Doppler spectrum image at the position of the mitral valve tip, to obtain the peak value of the velocity of the mitral annulus based on the third Doppler spectrum image at the position of the annulus, and to obtain the index by dividing the peak value of the blood flow velocity at the position of the mitral valve tip by the peak value of the velocity of the mitral annulus.

* * * * *